United States Patent
Brummelkamp et al.

(10) Patent No.: US 10,351,845 B2
(45) Date of Patent: Jul. 16, 2019

(54) ASSAYS TO IDENTIFY GENETIC ELEMENTS AFFECTING PHENOTYPE

(71) Applicant: STICHTING HET NEDERLANDS KANKER INSTITUUT-ANTONI VAN LEEUWENHOEK ZIEKENHUIS, Amsterdam (NL)

(72) Inventors: Thijn Reinout Brummelkamp, Amsterdam (NL); Joppe Daniël Maria Nieuwenhuis, Amsterdam (NL); Lucas Tilmann Jae, Amsterdam (NL); Markus Brockmann, Amsterdam (NL); Vincent Arthur Blomen, Amsterdam (NL); Matthijs Raaben, Amsterdam (NL)

(73) Assignee: STICHTING HET NEDERLANDS KANKER INSTITUUT-ANTONI VAN LEEUWENHOEK ZIEKENHUIS, Amsterdam (NL)

( * ) Notice: Subject to any disclaimer, the term of this patent is extended or adjusted under 35 U.S.C. 154(b) by 0 days.

(21) Appl. No.: 15/577,653

(22) PCT Filed: May 27, 2016

(86) PCT No.: PCT/NL2016/050381
§ 371 (c)(1),
(2) Date: Nov. 28, 2017

(87) PCT Pub. No.: WO2016/190743
PCT Pub. Date: Dec. 1, 2016

(65) Prior Publication Data
US 2018/0163197 A1   Jun. 14, 2018

(30) Foreign Application Priority Data
May 28, 2015  (NL) .................................... 2014877

(51) Int. Cl.
*C12Q 1/68* (2018.01)
*C12N 15/10* (2006.01)
*C12N 15/01* (2006.01)
*C12Q 1/6886* (2018.01)
*G01N 33/574* (2006.01)

(52) U.S. Cl.
CPC ......... *C12N 15/1051* (2013.01); *C12N 15/01* (2013.01); *C12N 15/1024* (2013.01); *C12N 15/1079* (2013.01); *C12Q 1/6886* (2013.01); *G01N 33/574* (2013.01)

(58) Field of Classification Search
None
See application file for complete search history.

(56) References Cited

FOREIGN PATENT DOCUMENTS

WO    2011/006145      1/2011
WO    WO-2016190743 A1   12/2016

OTHER PUBLICATIONS

International Search Report, International Patent Application No. PCT/NL2016/050381, dated Sep. 6, 2016.
Zdenek Andrysik et al. "A Genetic Screen Identifies TCF3/E2A and TRIAP1 as Pathway-Specific Regulators of the Cellular Response to p53 Activation" Cell Reports, vol. 3, No. 5, May 1, 2013, pp. 1346-1354.
Gowen, Benjamin G. et al. "A forward genetic screen reveals novel independent regulators of ULBP1, an activating ligand for natural killer cells", ELIFE, vol. 26, Nov. 13, 2015, p. 374.
Carette et al. Haploid genetic screens in human cells identify host factors used by pathogens. Science 326(5957):1231-1235 (2009).
PCT/NL2016/050381 International Preliminary Report on Patentability dated Dec. 7, 2017.
Brummelkamp. Haploid Genetics in Human Cells to Unravel Disease Networks. University of Edinburgh 2016 (78 pgs) (May 4, 2016).
Brummelkamp. Unraveling disease-linked networks with haploid genetics. CeMM 2016, Vienna (81 pgs) (Apr. 4, 2016).

*Primary Examiner* — James Martinell
(74) *Attorney, Agent, or Firm* — Wilson Sonsini Goodrich & Rosati

(57) ABSTRACT

The present invention comprises generally applicable methods for identifying endogenous physiologically relevant genetic elements that affects a intracellular phenotype of interest. In the methods, non-living cells that have been subjected to a mutagenesis treatment are sorted based on phenotype and analyzed to identify the genetic element. By use of these methods, elements previously unknown to be involved in a phenotype can be identified, for example in relationship to health conditions, external stress or drug response, in particular in cancer.

20 Claims, 23 Drawing Sheets
Specification includes a Sequence Listing.

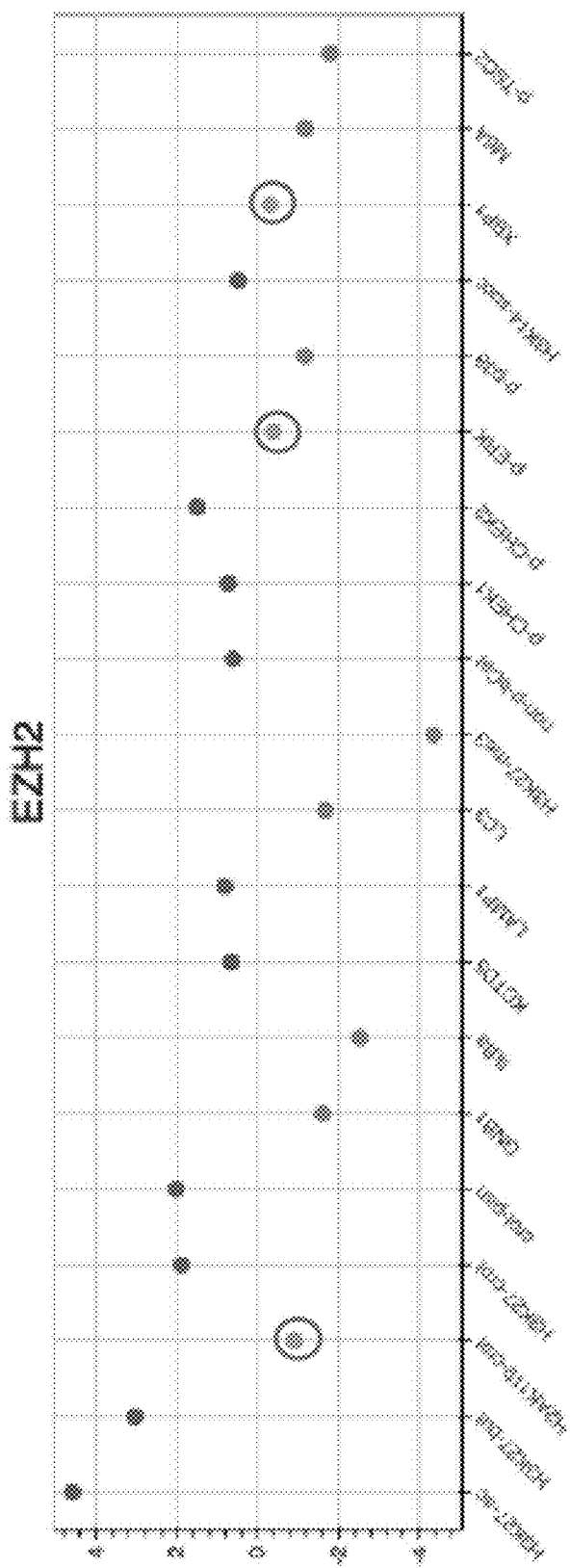
FIG. 13 - Continued

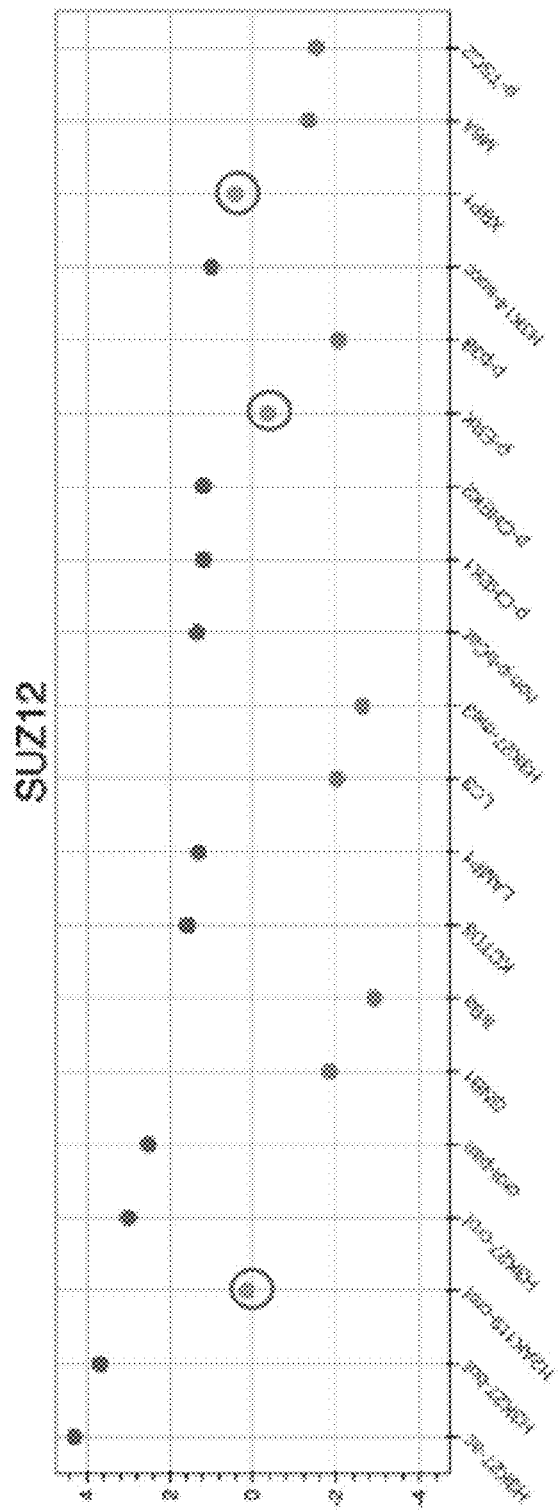
FIG. 13 - Continued

SEQUENCE LISTING

<160> NUMBER OF SEQ ID NOS: 14

<210> SEQ ID NO 1
<211> LENGTH: 22
<212> TYPE: DNA
<213> ORGANISM: Unknown
<220> FEATURE:
<223> OTHER INFORMATION: primer

<400> SEQUENCE: 1
ggtctccaaa tctcggtgga ac                                              22

<210> SEQ ID NO 2
<211> LENGTH: 49
<212> TYPE: DNA
<213> ORGANISM: Unknown
<220> FEATURE:
<223> OTHER INFORMATION: primer

<400> SEQUENCE: 2
atcgtatgcc gtcttctgct tgactcagta gttgtgcgat ggattgatg                 49

<210> SEQ ID NO 3
<211> LENGTH: 49
<212> TYPE: DNA
<213> ORGANISM: Unknown

<220> FEATURE:
<223> OTHER INFORMATION: primer

<400> SEQUENCE: 3
atcgtatgcc gtcttctgct tgactcagta gttgtgcgat ggattgatg                49

<210> SEQ ID NO 4
<211> LENGTH: 44
<212> TYPE: DNA
<213> ORGANISM: Unknown
<220> FEATURE:
<223> OTHER INFORMATION: primer

<400> SEQUENCE: 4
aatgatacgg cgaccaccga gatctgatgg ttctctagct tgcc                    44

<210> SEQ ID NO 5
<211> LENGTH: 21
<212> TYPE: DNA
<213> ORGANISM: Unknown
<220> FEATURE:
<223> OTHER INFORMATION: primer

<400> SEQUENCE: 5
caagcagaag acggcatacg a                                             21

<210> SEQ ID NO 6
<211> LENGTH: 33
<212> TYPE: DNA
<213> ORGANISM: Unknown
<220> FEATURE:
<223> OTHER INFORMATION: primer

<400> SEQUENCE: 6
ctagcttgcc aaacctacag gtggggtctt tca                                33

<210> SEQ ID NO 7
<211> LENGTH: 41
<212> TYPE: DNA
<213> ORGANISM: Unknown
<220> FEATURE:
<223> OTHER INFORMATION: primer

<400> SEQUENCE: 7
aatggactat catatgctta ccgtaacttg aaagtatttc g                       41

<210> SEQ ID NO 8
<211> LENGTH: 43
<212> TYPE: DNA
<213> ORGANISM: Unknown
<220> FEATURE:
<223> OTHER INFORMATION: primer

<400> SEQUENCE: 8
ctttagtttg tatgtctgtt gctattatgt ctactattct tcc                     43

<210> SEQ ID NO 9
<211> LENGTH: 88
<212> TYPE: DNA
<213> ORGANISM: Unknown
<220> FEATURE:
<223> OTHER INFORMATION: primer
<220> FEATURE:
<221> NAME/KEY: misc_feature
<222> LOCATION: (59)..(64)
<223> OTHER INFORMATION: n is a, c, g, or t

```
<400> SEQUENCE: 9
aatgatacgg cgaccaccga gatctacact ctttccctac acgacgctct tccgatctnn    60
nnnntcttgt ggaaaggacg aaacaccg                                        88

<210> SEQ ID NO 10
<211> LENGTH: 83
<212> TYPE: DNA
<213> ORGANISM: Unknown
<220> FEATURE:
<223> OTHER INFORMATION: primer

<400> SEQUENCE: 10
caagcagaag acggcatacg agatgtgact ggagttcaga cgtgtgctct tccgatcttc    60
tactattctt tcccctgcac tgt                                            83

<210> SEQ ID NO 11
<211> LENGTH: 25
<212> TYPE: DNA
<213> ORGANISM: Unknown
<220> FEATURE:
<223> OTHER INFORMATION: primer

<400> SEQUENCE: 11
caccgaggtg ccgccgacgt tgagt                                          25

<210> SEQ ID NO 12
<211> LENGTH: 25
<212> TYPE: DNA
<213> ORGANISM: Unknown
<220> FEATURE:
<223> OTHER INFORMATION: primer

<400> SEQUENCE: 12
caccggacgt tgagtcggac ccact                                          25

<210> SEQ ID NO 13
<211> LENGTH: 20
<212> TYPE: DNA
<213> ORGANISM: Unknown
<220> FEATURE:
<223> OTHER INFORMATION: primer

<400> SEQUENCE: 13
ggtatgtcgg gaacctctcc                                                20

<210> SEQ ID NO 14
<211> LENGTH: 25
<212> TYPE: DNA
<213> ORGANISM: Unknown
<220> FEATURE:
<223> OTHER INFORMATION: primer

<400> SEQUENCE: 14
caccgaggat ttcgggtccc ggcac                                          25
```

ASSAYS TO IDENTIFY GENETIC ELEMENTS AFFECTING PHENOTYPE

PRIOR ART

Mutagenesis-based genetics has been used to study numerous different phenotypes. This powerful approach has identified genes needed for cell division (by searching for temperature-sensitive mutant yeast strains), early embryonic development (by screening for aberrant embryogenesis in flies) and programmed cell death (by studying cell death during development in C. elegans). Typically, an organism of choice is mutagenized and resulting offspring (sometimes after crossing(s)) is examined for phenotypes of interest.

It is critical in these cases to have access to viable mutant organisms to link the mutation of interest to the observed phenotype. In some cases the phenotype is lethal or decreases fitness (for example early developmental defects in Drosophila or cell division phenotypes in yeast). For such phenotypes, the causative mutations can be mapped in parents of the affected offspring or one can make use of temperature-sensitive alleles.

In general, one major problem in genetic screens is the presence of high levels of "noise" hampering significantly the identification of relevant candidates/genes related to the phenotype under study. Examples of such noise include the presence of a large number of potential hits that turn out not to be relevant, not reproducible or the like. Genetic screens thus not only require laborious experimentation and follow-up studies to find, amongst the many potential hits identified the relevant ones, but it also means that only very strong signals are likely to picked-up. Signals/hits that are less strong in the screen but that are relevant in relationship to the phenotype under study are missed.

In light of this, methods for high-throughput approaches, which allow for reliable genetic screens, for example in in eukaryotic systems, based on phenotypical traits that are manifested intracellularly (i.e. that are present in a cell or in a cell of an organism), or that can only be detected intracellularly (requiring access to the interior of the cell), are highly desirable, but are not yet readily available for muta-genesis-based genetics or other genetic screens carried out on large populations (pools, complex pools) of modified cells (heterogeneous populations with respect to the presence of mutations).

In particular there is a clear need in the art for reliable, efficient and reproducible methods that allow the straight-forward identification of unknown genetic elements (genes, exons, introns, SNPs and so on) that affect the phenotype of a cell or organism (i.e. that are involved in changing or providing a certain trait of a given character), including such genetic elements that would be difficult to identify in prior art genetic screens due to the high level of noise. This is in particular relevant for those phenotypes that are manifested intracellularly (or that can only be detected intracellularly). Having such methods would at the same time allow the identification of the cellular elements related to these genetic elements (including but not limited to the proteins expressed or modulated by such genetic elements, the activity of such cellular elements and/or related biomolecules (e.g. lipids, other proteins or enzymes, metabolites) modulated or created by these cellular elements).

Accordingly, the technical problem underlying the present invention can be seen in the provision of such method for complying with any of the aforementioned needs. The technical problem is solved by the embodiments characterized in the claims and herein below.

It is an object of the current invention to provide for a method, or an improved method, that allows the identification of a genetic element, in particular an endogenous genetic element, that affects a phenotype, preferably a phenotype that is (at least in part) manifested intracellularly and/or that is or needs to be detected intracellularly.

It is a further object of the current invention to provide for such method that allows the identification of cellular elements related to the genetic element that affects the phenotype.

It is an object of the current invention to provide for a method that allows the identification of one or more than one genetic element (and/or cellular elements related thereto), from a large population of cells that have subjected to a mutagenesis treatment, wherein each genetic element alone, or in combination, affects a phenotype that is manifested intracellularly and/or that is detected intracellularly.

It is an object of the current invention to provide for a forward genetic screen that allows the identification of a genetic element (and/or cellular elements related thereto) in particular an endogenous genetic element that affects a phenotype that is manifested intracellularly and/or that is detected intracellularly.

It is an object of the current invention to provide for such forward genetic screens that is not or to a lesser extent hampered by relative high noise over relevant hits ratio's, in other words that show low levels of noise, i.e. not relevant hits. This thus allows for a straightforward identification of relevant genetic elements and may prevent or reduce additional laborious confirmation studies.

It is an object of the current invention to provide for the above in eukaryotic cells, for example, but not limited to human cells, including cells carrying disease-causing mutations, for example human cancer cells.

It is also an object of the current invention to provide for a method for identifying a modulator, for example a drug, of a gene product, in particular and endogenous gene product, encoded by a candidate gene that affects a phenotype of a cell.

It is an object of the current invention to provide for a method of establishing or analyzing biological pathways, for identifying genes involved in disease, for example, but not limited to cancer, for studying drug-target interaction, for studying drug-drug interaction, or to analyze suppression or modulation of a phenotype, preferably a phenotype associated with a disease, including cancer.

These and other objects are solved with the methods of the invention disclosed herein.

DEFINITIONS

Figure 1A:
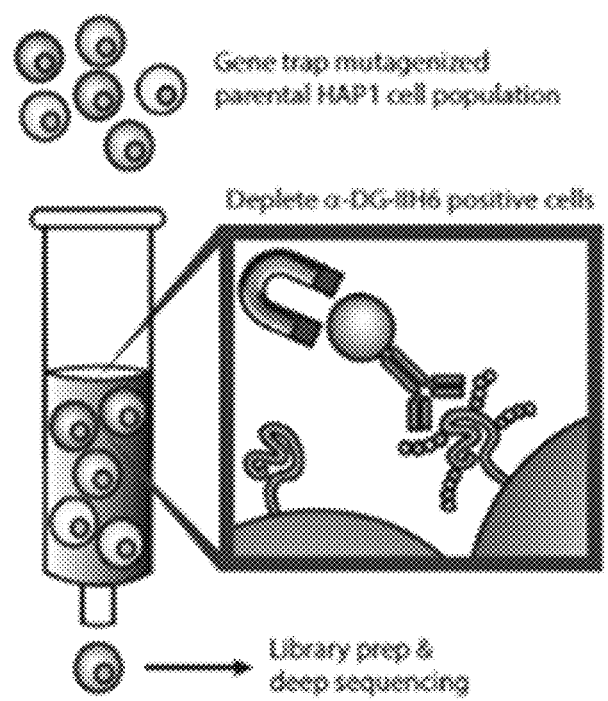
FIG. 1A. Depiction of how an antibody that recognizes glycosylated dystroglycan at the cell surface is used to enrich for mutants that lacked the respective antigen at the cell surface. Living cells were sorted, expanded in culture and subjected to deep-sequencing of the gene-trap insertion sites.
Figure 1B:
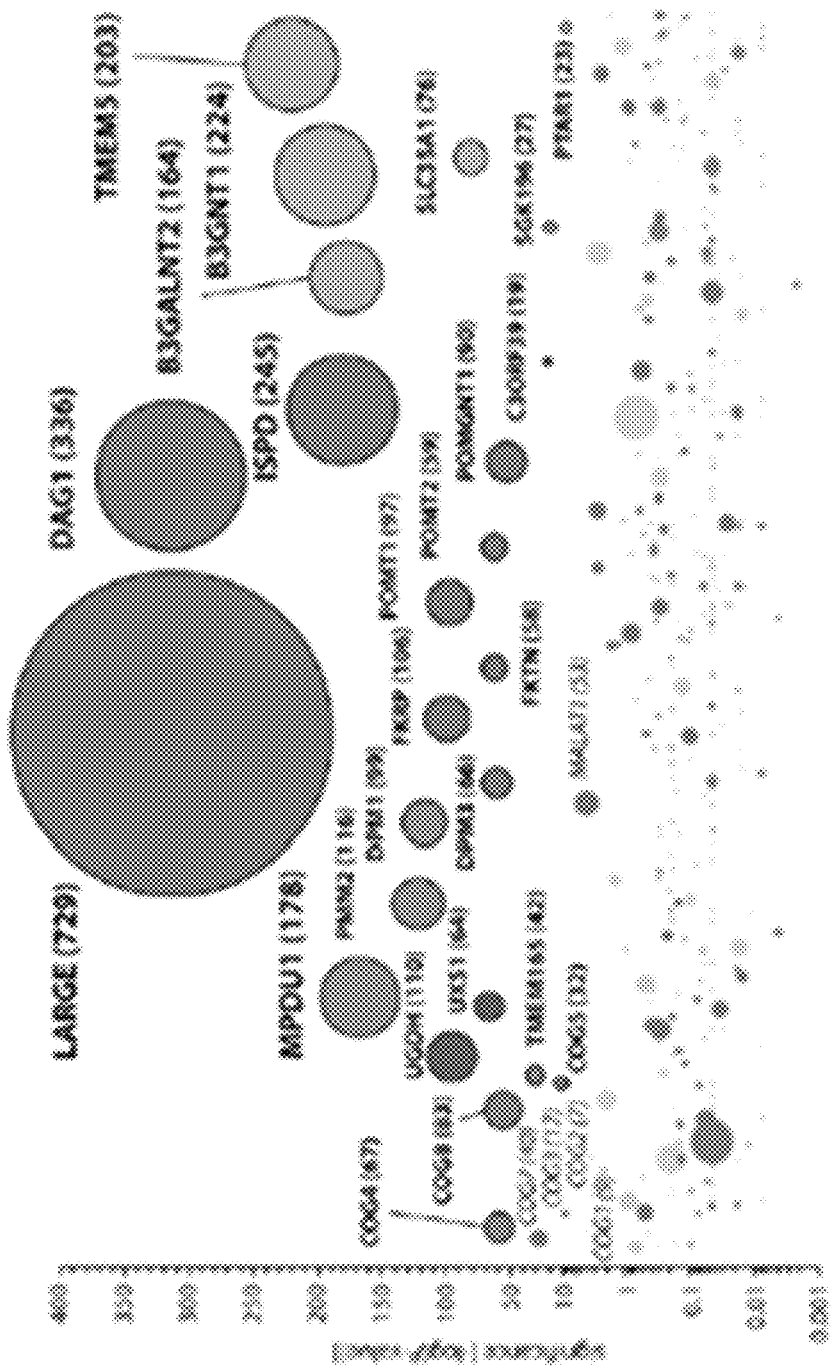
FIG. 1B. A plot showing the genes that were significantly enriched for mutations in the viable selected cell population compared to an unselected population.
Figure 1C:
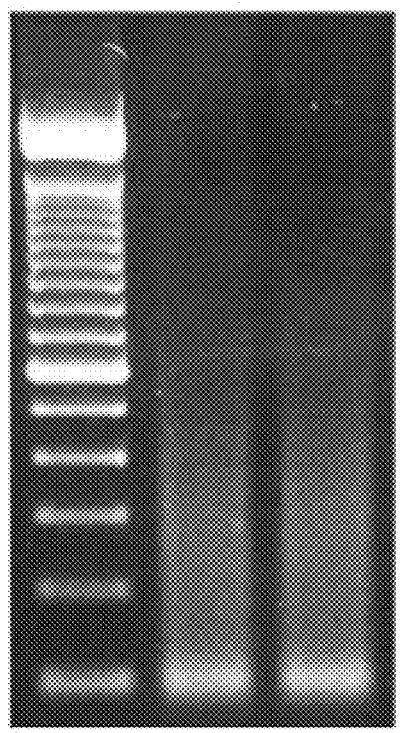
FIG. 1C. Recovery of the gene-trap integration sites from fixed non-expanded cells yields a typical smear of LAM PCR amplified DNA assessed by agarose gel electrophoresis.
Figure 1D:
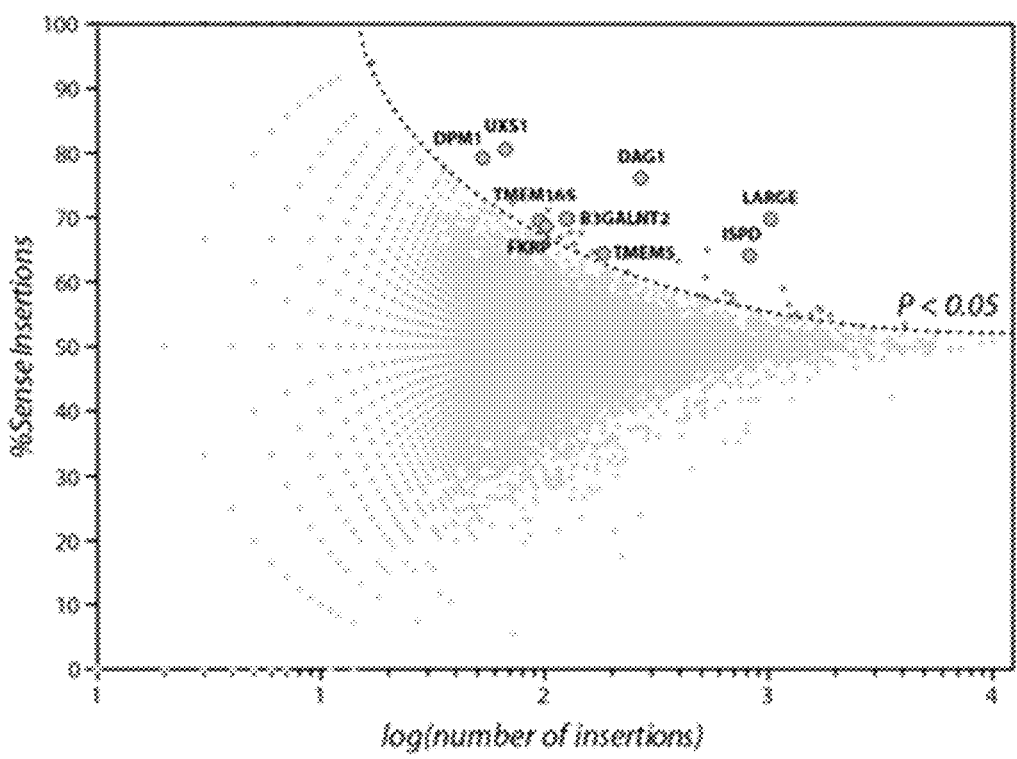
FIG. 1D. Plot depicting the distribution of sense and antisense gene-trap integrations recovered in genes following deep sequencing of fixed non-expanded cells that were selected to lack cell surface dystroglycan. Dystroglycan (DAG1) and genes required for the glycosylation of dystroglycan that were enriched for sense orientation integrations are labeled.

In the following description and examples, a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

As used herein, the term "common scientific terms", unless defined otherwise, refers to technical and scientific terms used herein which have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described and the practice of conventional techniques in molecular biology, biochemistry, computational chemistry, cell culture, recombinant DNA, bioinformatics, genomics, sequencing and related fields are well-known to those of skill in the art.

As used herein, the singular forms "a," "an" and "the" include plural referents unless the context clearly dictates otherwise. For example, a method for isolating "a" DNA molecule includes isolating a plurality of molecules (e.g. 10's, 100's, 1000's, 10's of thousands, 100's of thousands, millions, or more molecules).

As used herein, and unless specifically stated or obvious from context, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

As used herein, the term "and/or" indicates that one or more of the stated cases may occur, alone or in combination with at least one of the stated cases, up to with all of the stated cases.

As used herein, with "At least" a particular value means that particular value or more. For example, "at least 2" is understood to be the same as "2 or more" i.e., 2, 3, 4, 5, 6, 7, 8, 9, 10, 11, 12, 13, 14, 15, . . . , etc.

As used herein, the terms "amplification" and "amplifying" refer to a polynucleotide amplification reaction, namely, a population of polynucleotides that are replicated from one or more starting sequences. Amplifying may refer to a variety of amplification reactions, including, but not limited to, polymerase chain reaction, linear polymerase reactions, nucleic acid sequence-based amplification, rolling circle amplification and like reactions. Typically, amplification primers are used for amplification, the result of the amplification reaction being an amplicon.

As used herein, the terms "comprising" and "to comprise", and their conjugations, refer to a situation wherein said terms are used in their non-limiting sense to mean that items following the word are included, but items not specifically mentioned are not excluded. It also encompasses the more limiting verb "to consist of".

As used herein, the term "crosslinking" refers to the action of reacting an agent with DNA at two different positions, such that these two different positions may be connected. Crosslinks may occur between DNA strands of the same (double stranded) DNA molecule and/or between DNA and protein. A crosslinking agent that may be advantageously used according to the invention is (para-)formaldehyde. Formaldehyde induces protein-protein and DNA-protein crosslinks. Formaldehyde thus may crosslink different DNA strands to each other via their associated proteins. The crosslinks may be reversed through a heating step, for example by incubating at 60° C. The crosslinking results in the formation of crosslinks between proteins and/or DNA, and allows the three-dimensional state of the DNA to largely remain unaltered.

As used herein, the term "expression level" of a gene refers to the amount of RNA transcript that is transcribed by a gene and/or the amount of protein that may be translated from an RNA transcript, e.g. mRNA. For example, for genes which encode a miRNA, the expression level may be determined through quantifying the amount of RNA transcript which is expressed, e.g. using standard methods such as quantitative PCR of a mature miRNA, microarray, or Northern blot. Alternatively, the expression level may also be determined through measuring the effect of a miRNA on a target mRNA.

As used herein, the term "expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi).

As used herein, the term "gene" refers to a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites.

As uses herein, the term genetic element refers to an element in a DNA or RNA molecule, i.e. a basic part of a DNA or RNA molecule, or a part considered as such by the skilled person. The genetic element may consist of one nucleotide or may comprise more than one nucleotide. In case a genetic element comprises more than one nucleotide, these nucleotides are adjacent nucleotides. A genetic element may thus, for example consist of any number of adjacent nucleic acids (e.g. at least/at most 1, 5, 10, 100, 1000, 10000, 100000, 1000000 nucleic acids in length) or may consist of different groups of such adjacent nucleic acids (e.g. the exons spatially separated). Within the context of the current invention, the genetic element is a part of a DNA or RNA molecule that, with the method according to the invention, is recognized as affecting the phenotype under study. The genetic element may be a (part of) a DNA molecule or RNA molecule, and may, for example, be present on a chromosome or episomal. In eukaryotes, the genetic element may, for example, be present in the nucleus, in the cytosol, or in any other organelle, including the mitochondria. The genetic element may be present naturally in the cells subjected to the method of the invention or may be a genetic element that has be introduced in these cells on purpose. However, preferably the genetic element is a genetic element that is endogenous to the cells used in the method of the invention (i.e. that originate from within the organism from which the cells are obtained and/or persist in the germ-line of the organism/cell). For example, the genetic element may be a single-nucleotide polymorphism (SNP) identified with a gene, wherein the method according to the invention identified the presence of the SNP as being associated with the phenotype under study. However, preferably the genetic element is a functional genetic element as generally recognized by the skilled person, including and preferred but not limited to a promoter, a gene, an intron, an exon, an enhancer, a non-coding RNA molecule, a repressor element and the like. Also contemplated are single-nucleotide polymorphisms (SNP), for example a SNP without an associated gene. A "cellular element" as used herein refers to any other element, in particular biomolecule in a cell that is not a DNA or RNA molecule. The term cellular element in this context refers to any other element in the cell not being a genetic element and includes but is not limited to the proteins, lipids, sugars and carbohydrates present in the cell, but also includes other metabolites and biomolecules present in the cell, organelle or membranes of the cell. As will be understood by the skilled person the identification of the genetic element with the method according to the invention may also allow for the identification of the related cellular element. For example in case the genetic element is (part of) a gene encoding a protein, the protein encoded by the gene is a corresponding cellular element. For example, in case the genetic element is (part) of a gene encoding a protein known to bind a specific lipid, the lipid may also be a corresponding cellular element. For example, in case the genetic element is a non-coding RNA, for example involved in RNA interference, a RNA comprising the complement of said non-coding RNA, and the protein encoded, are corresponding cellular elements.

As used herein, the term "gene product" refers to molecules consisting of a chain of nucleotides or amino acids, without reference to a specific mode of action, size, three-dimensional structure or origin that are the products of transcription and translation of a certain gene.

As used herein, the terms "high throughput sequencing" and "next generation sequencing" and "deep sequencing" refer to sequencing technologies that are capable of generating a large amount of reads, typically in the order of many thousands (i.e. tens or hundreds of thousands) or millions of sequence reads rather than a few hundred at a time. High throughput sequencing is distinguished over and distinct from conventional Sanger or capillary sequencing.

As used herein, "Less than" or "up to" and the like means the range from zero up to and including the value provided. For example, "less than 10" or "up to 10" is understood as 0, 1, 2, 3, 4, 5, 6, 7, 8, 9, or 10.

As used herein, the term "phenotype" refers to at least one observable characteristic or trait of an organism or cell of an organism such as its morphology, development, biochemical or physiological properties, phenology, behavior, and products of behavior.

Phenotypes result from the expression of the genes of an as well as the influence of environmental factors and the interactions between the two. Although a phenotype is the ensemble of observable characteristics displayed by an organism, the word phenome is sometimes used to refer to a collection of traits and their simultaneous study is referred to as phenomics. As used herein "a genetic element that affects a phenotype" thus refers to a genetic element as defined herein that influences the manifestation of said phenotype, i.e. that is a modulator of/modulates/influences said phenotype. The genetic element may for example be involved in causing or promoting a first trait of the phenotype (or first trait of a character), of may be involved in repressing another trait of the same phenotype. Inducing changes in such genetic element, for example, as the consequence of the mutagenesis treatment as described herein, may thus cause the modification of such phenotype (the trait may change). The method of the invention thus allows for the identification of such genetic elements based on the detection of the/a affected (changed, modified, altered) phenotype (i.e. the manifestation of a phenotypic trait, a distinct variant of a phenotypic characteristic or character of an organism or cell).

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter.

As used herein, the term "sequencing" refers to determining the order of nucleotides (base sequences) in a nucleic acid sample, e.g. DNA or RNA.

As used herein, the term "trait", in the context of biology, refers to a trait that relates to any phenotypical distinctive character of an individual member of an organism, or of an individual cell, in comparison to (any) other individual member of the same organism, or of (any) other individual cell. For example, in the current invention traits (preferably of the same character) of cells (from the same organism) are compared. Within the context of the current invention the trait can be inherited, i.e. be passed along to next generations of the organism by means of the genetic information in the organism. As used herein, the terms "trait of the same character" and "trait of said character" refer to anyone of a group of at least two traits that exist (or became apparent) for a character. For example, in case of the character "color of the flower", phenotypical manifestations (traits) might comprise blue, red, white, and so on. In the above example blue, red and white are all different traits of the same character.

DETAILED DESCRIPTION OF THE INVENTION

The goals and objects of the invention are solved with the methods of the invention characterized herein in the claims, clauses, description, drawings and examples.

The method of the invention is a high-throughput approach that provides a reliable genetic screen, for example in eukaryotic systems, based on phenotypical traits that, preferably, are manifested intracellularly, or that can only be detected intracellularly. The method concerns mutagenesis-based genetics carried out on/with large populations of cells, i.e. pools or complex pools of cells. Preferably the pool of cells consists of isogenic cells or are cells of the same type (for example, derived from the same cell line). The cells in the pool may be subjected to a mutagenesis treatment. These treatments may be as such that a heterogeneous populations of cells are obtained with respect to the mutations introduced in the cells. In other words, after the treatment, different cells within the pool may comprise various mutations, at various positions and in various numbers. For example, a first cell in the population may comprise 5 mutations after such mutagenesis treatment, for example a mutation in a gene A, a gene B, an exon C, an intron D and a gene E whereas another cell may comprise the same of a different number of mutations and at different positions in the genome. A corresponding situation can be envisaged in case of a treatment modifying gene expression and as detailed herein. Next, the cells in the treated pools are (preferably after fixation and permeabilization of the cells) sorted based on the phenotype under study; for example in a first population not having the defined (or desired or pre-determined) trait of a given character and a second population having the trait. Based on the sorting, the underlying genetic element, involved in the phenotype (character, trait) can be identified.

In particular the method provides for a reliable, efficient and reproducible method that allows the identification of unknown genetic elements that affect the phenotype of a cell or organism, in particular with respect to those phenotypes that are manifested intracellularly/that can only be detected intracellularly.

In a first aspect a method is provided for identifying a genetic element that affects a phenotype of a cell, preferably wherein the phenotype is manifested intracellularly (i.e. can or must be detected in the cell, for example using a probe that detects the phenotype intracellularly). The method for identifying a genetic element that affects a phenotype of a cell comprises several steps, as described herein below. The steps of the invention comprise:

(a) Subjecting a pool of cells to mutagenesis treatment;

(b) Fixating the pool of cells, preferably with a fixation reagent, and optionally a cross-linking agent, and permeabilizing the pool of cells, preferably with a permeabilization reagent (i.e. subjecting at least part of the cells in the treated pool of cells to fixation and permeabilization, and optionally to cross-linking);

(c) Treating the pool of cells with one or more detectable probe(s), preferably an antibody or a RNA probe, that specifically detects the affected (or manifested) phenotype;

(d) Sorting the cells based on the detection of at least one of the one or more detectable probe(s) to obtain one or more population(s) of cells;

(e) Optionally, de-crosslinking the cells in each of the obtained populations of cells; and (f) Sequencing at least part of the cells of at least part of the obtained populations of cells to identify a genetic element that affects the phenotype of the cell.

Although the successive steps of the method according to the invention may be performed consecutively (i.e. without any other steps being performed between the steps described herein), the invention is not limited thereto; additional steps may be performed prior to or after any of the steps of the inventive method disclosed herein or between two successive steps of the method of the invention.

The method according to the invention is preferably performed in vitro, although in principle certain steps of the method may be performed in, for example, in vivo, for example, in a plant or non-human animal. In particular in embodiments wherein the method includes exposing the living cells to environmental conditions (e.g. stress, growth conditions, drugs and metabolites, metabolites produced by other cells, and the like) it may be desirable to perform at least part of the method in vivo.

The method of the invention only requires one pool of cells, but more than one pool of cells may be used sequentially or in parallel, i.e. undergo the various steps of the method after the first pool of cells, or at the same time (in a parallel experiment).

Within the context of the current invention the term in vitro is used to indicate a method (step) performed with cells and that is performed outside the normal biological context of these cells, for example in a tissue or cell culture (system) using artificial culture medium. Within the context of the current invention, the term also encompass ex vivo (i.e. experimentation done in or on tissue from an organism in an external environment (outside the body of the animal). In vivo studies are those conducted in animals or plants. The skilled person will understand that the method according to the invention can also be used for unicellular organisms and/or organism that consist of a limited amount of cells (e.g. bacteria and fungi). Preferably the method according to the invention is performed using eukaryotic cells.

The method of the invention allows for the identification of a genetic element. Identification, with in the context of the current invention refers to establishing, recognizing and/or associating a certain genetic element in relationship to the affected phenotype. The method allows for the identification of the genetic elements that are involved in or causes or modifies the phenotype, e.g. causes the manifestation of a trait of the character. As exemplified in the Examples herein below, the method according to the invention allows to establish, recognize or associate genetic elements in relationship to a given phenotype. The genetic element may be a known genetic element, or even a known genetic element in relationship to the given phenotype, but the method in particular allows the identification of genetic elements that are either unknown or that where not known to be related to/involved in the given phenotype.

The genetic element that is identified may be any genetic element that is present in the cell. The genetic element may be a DNA genetic element or a RNA genetic element and it may, for example, be present on a chromosome or episomal. In eukaryotes, the genetic element may, for example, be present in the nucleus, in the cytosol, or in any other organelle, including the mitochondria. The genetic element may be present naturally in the cells subjected to the method of the invention or may be a genetic element that has be introduced in these cells on purpose. However, preferably the genetic element is a genetic element that is endogenous to the cells used in the method of the invention (i.e. that originate from within the organism from which the cells are obtained and/or persist in the germ-line of the organism/cell). For example, it may be present in/or the chromosomes in the cell.

The genetic element may consist of any number of adjacent nucleic acids (e.g. at least/at most 1, 5, 10, 100, 1000, 10000, 100000, 1000000 nucleic acids in length) as long as it is identified in context with the given phenotype.

For example, the genetic element may be a single-nucleotide polymorphism (SNP) identified with a gene, wherein the method according to the invention identified the presence of the SNP as being associated with the phenotype under study. However, preferably the genetic element is a functional genetic element as generally recognized by the skilled person, including and preferred but not limited to a promoter, a gene, an intron, an exon, an enhancer, a non-coding RNA molecule, a repressor element and the like. Also contemplated are single-nucleotide polymorphisms (SNP), for example a SNP without an associated gene.

As will be understood by the skilled person the identification of the genetic element can subsequently be used to identify further cellular elements. For example, once a gene is identified with the method according to the invention, also the protein encoded by such gene is identified by the method according to the invention. In addition, when, for example, the protein encoded by the identified gene, is an enzyme producing a metabolite, the metabolite can be identified with the method according to the invention. Another example is when the protein is, for example, involved in post-translation modification of other protein and/or lipids (e.g. a kinase) or is involved in epigenetic modifications; the target of such protein may also be identified with the method according to the invention. Another example is when the gene encodes a non-translated transcript, such as a micro-RNA that affects expression of another gene, the target of such a transcript may also be identified with the method according to the invention. Such identification of cellular elements, in particular proteins and enzymes, including for example methylating enzymes (of DNA and RNA), is specifically contemplated as belong to the invention described herein.

The method disclosed herein allows for the identification of a genetic element (and corresponding cellular element(s)) (e.g. protein or metabolite) that affects a phenotype in a cell. The method according to the invention involves subjecting cells to a mutagenesis treatment, for example, using chemical mutagenesis, a gene-trap or using a CRISPR library of guide RNA sequences (discussed in detail herein below). In a preferred embodiment, the treatment allows, for example, for the introduction of numerous different and genome-wide mutations in the pool of cells subjected to the treatment. In other words, in the pool of cells (i.e. in the same sample), the cells will carry many different (for example random) mutations as the consequence of the treatment of the cells, and wherein different cells carry different mutations.

Next, the cells are sorted based on at least one given phenotype in order to identify the genetic element that causes or is associated with the given phenotype, i.e. which affects the phenotype. In other words, the genetic element identified with the method according to the invention is involved in causing or associated with the phenotype and/or traits of the character considered. For example, the genetic element identified may be a gene that as the consequence of, for example, the mutagenesis treatment, has been mutated, causing, for example, the non-expression of the corresponding protein, which, in turn, causes a certain trait of a given character, a phenotype. The genetic element, in this case the gene, is thus involved in establishing the various traits of the character (one trait being the consequence of non-expression of the genetic element, in this case the gene, whereas, consequently another trait is related to expression of the genetic element), and thus affects the phenotype within the context of the current invention.

Within the context of the current invention a phenotype is a trait (a distinct variant of a phenotypic characteristic) of a certain character that is manifested by the organism or cell. The trait may be observed directly or indirectly, in the latter case the trait being detectable using additional means (for example by using an antibody or any other means or functional assay). For example, the character may be "response to a drug", possible traits being "resistant" or "sensitive". Another character may be abundance of a protein, possible traits being "low", "normal" or "high". A third example is the trait "cellular kinase activity of a protein", possible traits being "no activity", "low activity" or "high activity". A final example is "phosphorylation status of a protein", again, with possible traits being, for example "not phosphorylated" or "phosphorylated". From the above the skilled person understand that a trait (or phenotype) may be considered in a qualitative manner (for example, no expression versus expression of a protein) or in a quantitative manner (no expression, low expression, normal expression, more than normal expression, high expression (or abundance)).

Examples of other preferred characters (and corresponding phenotype/traits) include but are not limited to: activity of a protein, abundance of a protein, abundance of a RNA, abundance of a metabolite, mitochondrial membrane potential, post-translational modification of a protein, number of lysosomes, shape of an organelle (for examples using a flow cytometer like IMAGESTREAM provided by Amnis), reactive oxygen species (ROS), number of peroxisomes or other organelles, Ca-flux or other cations, protein conformation (using conformational specific antibody screens (e.g. detecting misfolded protein)), kinase activity, phosphatase activity, and so on, are other common protein activities that can be listed.

For the method according to the invention the phenotype (character/trait) may be manifested or be detectable anywhere in or on the cell (for example at the cell surface, in the cell membrane (inner and/or outer layer), in the cytosol, in the membrane or lumen of an organelle, and the like). The phenotype may be detectable directly or indirectly. However, and in contrast to methods known in the art, the method according to the invention is in particularly suitable for a phenotype (character/trait) that is manifested or detectable intracellularly (i.e. anywhere except for the cell surface). With the method according to the invention it becomes possible to detect such intracellular phenotype in an individual cell in a pool of cells (by actually killing (by permeabilizing and fixing) the cells in the pool of cells), sorting the cells from the pool of cells (based on the phenotype for which the genetic element is sought) and, using sequencing technology, identify the genetic element(s) that are involved in or related to the phenotype. In a preferred embodiment, the phenotype is a phenotype that is manifested intracellularly, in particular that can be detected intracellularly, for example after fixating and permeabilizing the pool of cells (discussed in more detail herein below). In a further preferred embodiment the phenotype is a phenotype that can only be detected intracellularly, and thus requires the provision of cells that have been subjected to fixation and permeabilization, and are, as the consequence of such treatment, non-viable. Preferably the phenotype to be detected intracellularly is a phenotype that can only be detected indirectly (i.e. is not visible to the eye, but requires additional means, such as probes, to detect the phenotype). In a particular preferred embodiment, the method according to the invention is a method for the identifying a genetic element (e.g. a promoter, gene, intron, exon, non-coding RNA) that affects a phenotype of a cell, wherein the phenotype is a phenotype that is (to be) detected intracellularly. In other words, the method according to the invention is in particular suitable for, but not limited to, those phenotypes that can be detected after treating the cells in a way that the phenotype can be detected intracellularly, for example by permeabilizing the cell membrane, allowing the entry of detection probes into the cell. Such treatment causes the cells to become non-viable (i.e. the cells cannot multiply in number anymore). In a further preferred embodiment, the method is for traits (phenotypes; characters) that can only be detected intracellularly, i.e. that require the permeabilization of the cell membrane before the trait (phenotype, character) can be detected, although the invention is not limited thereto. In such embodiment, the traits (phenotype, character) cannot be detected from outside of the cell (i.e. the trait (phenotype, character) is only detectable intracellularly).

In an initial step of the method described herein a pool of cells is subjected to a mutagenesis treatment (e.g. as detailed herein). Although not limited thereto, the pool of cells may preferably be cells obtained from one and the same individual organism, although also a pool of cells may be used that comprise cells of different origin. The pool of cells may be primary cells but for practical reason preferably a cell line is used. The cell line may be an established cell line (for example, a commercially available cell line). The number of cells in the pool is not critical for the method described herein, but the pool may typically comprise 1 million to several hundreds of millions of cell, depending on for example, the cells and or the method of treatment used in this initial step.

The term mutagenesis treatment is well-known in the art and relates to a treatment that introduces changes in the original genetic information (DNA) present in the cell, for example by insertion, deletion or substitution of one or more nucleotides. The mutation may comprise the change of only one nucleotide or may comprise many adjacent nucleotides (e.g. by deletion or by insertion of additional nucleotides). Within the context of the current invention, the mutagenesis treatment preferably causes genome wide deletions, insertions or substitutions i.e. may cause mutations at different positions throughout the genome present in the cell subjected to the treatment. The mutation treatment preferably introduces mutations in a random or semi-random fashion, i.e. are the treatment is not a treatment specifically aiming a, for example one, predetermined genetic element. Also contemplated is the use of library comprising means wherein each mean introduces a specific mutation at a specific location, and wherein the means in the library together introduce genome wide mutations (i.e. at different positions throughout the genome).

The mutagenesis treatment used in this initial step is preferably, but not limited thereto, a treatment that introduces many different mutations throughout the genome. In other words, the mutagenesis treatment according to the method of the invention is, preferably, a treatment that introduces many different mutations and at many different locations throughout the genetic material present in the cell that are subjected to the treatment. As a consequence a pool of cells is obtained in which one cell may have different mutations as compared to another cell in the same pool of cells, and wherein a cell may have more than one mutation and at different positions in the genetic material present in the cell. In other words, the mutagenesis treatment is a treatment that introduces mutations at more than one position, i.e. which provides cell carrying different mutations when compared with each other. For example, the mutagenesis treatment may be a treatment that randomly or semi-randomly introduces mutations and consequently may affect different genetic elements present in the cell. Alternatively, mutagenesis may be provided by using a (large) number of mutagens that each aimed at a specific target (e.g. using CRISPR technology). By treating with such a library also cells will be obtained each carrying different (in place and number) mutations. With the mutagenesis treatment the pool of cells thus becomes a heterogeneous pool of cells with respect to the presence of mutations in the individual cells and as compared to the non-treated pool of cells; i.e. an heterogeneously mutagenized pool of cells.

Indeed one objective is providing a method of the invention that allows to identify (new) genetic elements that are involved in a given phenotype. In that respect the method is to be considered to relate to a forward genetic screen, i.e. determining a genetic basis responsible for, involved in or associated with a given (predetermined) phenotype. Thus, the method according to the invention may also be considered a method for determining a genetic element that is responsible for, involved in, or associated with, a phenotype, e.g. a predetermined phenotype. The method first detects or determines a phenotype and next identifies the genetic element affecting the phenotype (forward genetic approach). Forward genetics is different from reverse genetics, which determines the function of a gene by analyzing the phenotypic effects of altered DNA sequences (e.g. by purposive and selectively introducing a mutation in a predetermined genetic element)./pct The skilled person is well-aware of the conditions and circumstance under which the pool of cells needs to be subjected to the mutagenesis treatment and/or a treatment that modifies gene expression. Such methods have been extensively described in various handbooks and are readily available to the skilled person. For example, methods as described in the Examples herein may be used.

In a next step of the method according to the invention, the pool of cells that has been subjected to the mutagenesis treatment are fixated and permeabilized. This may be done in one step (using one compostion both fixing and permeabilizing the cells, or may be done in separate steps using separate compositions. The skilled person in well aware of means and manners for fixating cells. Fixating may include cross-linking, but also may be done with non-cross-linking agents. Thus in one embodiment, and optionally, the fixating includes cross-linking. In another embodiment the cells are fixated, cross-linked and permeabilized. In other embodiment the cells are fixated and permeabilized. This may be done in one and the same treatment or in separate treatments. By fixation of the cells autolysis and/or putrefaction is prevented, thus preserving the cell components. In particular, the fixation of the cells allows for the later extraction and subsequent sequencing of (cellular) DNA and/or RNA.

In the art many different methods or protocols are available for fixation of cells, including such pools of cells as used in the method of the current invention. For example, fixation may be performed using protocols based on the use of crosslinking fixatives such as aldehydes (crosslinking fixatives act by creating covalent chemical bonds between proteins in the cell) or fixation may be performed using protocol based on the use of precipitating fixatives such as alcohols (e.g. as described by Smith et al. Anal Biochem. 1987; 160(1):135-8; precipitating fixatives act by reducing the solubility of protein molecules and (often) by disrupting the hydrophobic interactions that give many proteins their tertiary structure). However, other methods for fixation of the cells may as well be used (including methods based on oxidizing agents, and HOPE (Hepes-glutamic acid buffer-mediated organic solvent protection effect) fixative (e.g. http://www.dcs-diagnostics.de/), reported to provide good preservation of protein antigens and good RNA and DNA yields and absence of crosslinking proteins.

In addition to the fixation of the cells, the cells are permeabilized. Fixation and permeabilization may be provided for in the same step and/or may use the same reagent. Again, the skilled person is well aware of means and methods to permeabilize the cells. Permeabilization may be required in order to detect intracellular and intra-organellar compounds (i.e. cellular elements) such as antigens or lipids and the like. For this the pool of cells must thus first be permeabilized, for example after fixation (but fixation and permeabilization may also occur at the same time).

Although in principle any type of reagent may be used to permeabilize the cells in the pool, two general types of reagents are commonly used: organic solvents (which may also be used for fixation), such as methanol, ethanol and acetone, and detergents such as saponin, Triton X-100 and Tween-20. The organic solvents dissolve lipids from cell membranes, making them permeable. Because the organic solvents also coagulate proteins, they can be used to fix and permeabilize cells at the same time. Saponin interacts with membrane cholesterol, selectively removing it and leaving holes in the membrane. Detergents such as Triton X-100 and Tween-20 are non-selective in nature (reviewed in detail by Jamur Methods Mol Biol. 2010; 588:63-6.).

As will be understood by the skilled person, by fixating and permeabilizing the cells in the pool, these cells lose the ability to divide and grow since the cells are not viable after the treatment of fixating and permeabilizing the cells. The method of the invention is thus in particular useful for, but not limited to, identifying genetic elements that affect a phenotype, wherein the detecting of the phenotype requires fixation and/or permeabilization of the cells.

In a next step of the method described herein, the fixed and permeabilized pool of cells is treated with one or more probes that can be detected and that can be used to (specifically) detect the affected (or manifested) phenotype (i.e. trait of a character) for which the genetic element is to be identified. As already discussed herein above, the trait may be a qualitative trait and/or a quantitative trait. In case the trait is a qualitative trait the probe can be used to detect either the presence or absence of the phenotype (trait). In case of a quantitative trait, the probe used may initially lead to a detectable signal in both cells that do and cells that do not have the given phenotype, but based on the level of the signal, cells will be qualified or disqualified for manifesting a given phenotype under study. For example, in case an antibody is used as a probe to detect the abundance of a protein, both cells that will have high levels of the protein and cells that will have low levels of the protein will be detected by the probe. Based on the level of abundance (e.g. low versus high), cells that display low abundance of the protein will be considered (and sorted) as not having the phenotype if the phenotype is defined as high abundance of the protein. High abundance may for example me defined as the 5, 10, 20 or 20% highest signal providing cells of the total pool of cells.

In the method of the invention one or more detectable probes may be used. The probes may be directed to the same phenotype, but may also be directed to detecting different phenotypes in the same experiment. Thus, there is also provided for a method to identify one or more than one genetic elements for more than one phenotype, in the same experiment (multiplex).

The method according to the invention may in particular be used for phenotypes that consist of more than one element. For example, the phenotype/trait may be defined as having high expression of a first protein and having low expression of a second protein. In such embodiment, the phenotype may thus be detected by a first probe that detects the first element of the phenotype and a second probe that detects the second element of the phenotype. Subsequent sorting based on, in this example, both probes than allows for obtaining the cells (from the pool of cells) that manifest the desired, defined, and/or given phenotype. Thus, the phenotype within the context of the current invention may be a phenotype comprising only one element, but may also be more complex in nature and comprise different elements, together defining the phenotype.

The probes used in this step of the method may be any probe that can suitable be used in detecting (an element of) the given phenotype. In a preferred embodiment the detectable probe is an antibody, an RNA probe or a DNA probe. As the skilled person knows, RNA probes are sequences of a variable length that are used to detect the presence of complementary nucleotide sequences in a sample. RNA probes may be labeled with modified nucleotides that can be detected by, for example, fluorescence or chemiluminescence. For example, one can make use of techniques including RNA Fluorescence in situ hybridization (RNA FISH). For example, one could use RNA probes against telomeres to quantify the abundance of telomeric DNA (e.g. as the phenotype affected). Alternatively, molecular beacons or RNA beacons can be used (Molecular beacons include stem-loop hairpin-structured oligonucleotides equipped with a fluorescence quencher at one end and a fluorescent dye (also called reporter or fluorophore) at the opposite end. This structure permits that beacon in the absence of their target complementary sequence does not fluoresce. Upon binding to targets, the beacons emit fluorescence, due to the spatial separation of the quencher and the reporter.) Molecular beacons can be used as detectable probes in the method according to the invention (see also Journal of Nucleic Acids Volume 2011 (2011), Article ID 741723), and can be obtained from different companies, such as Eurogentec. In general, these RNA probes are used to quantify RNA molecules such as mRNA molecules. They find there targets through hybridization and can be equipped with a fluorophore or something else (see for example, Klemm et al. Nat Methods. 2014 May; 11(5):549-51.doi: 10.1038/nmeth.2910).

Suitable antibodies include, but are not limited to, antibodies that detect a certain protein, antibodies that specifically detect the presence or absence of a specific post-translational modification (e.g. a phosphospecific antibody), or antibodies that specifically detects a protein tertiary structure. Other preferred probes include, but are not limited to antibody mimetics (such as avimers, affibody molecules and the like), Biotin/Streptavidin-based probes, Antibody-like Protein-Capture Agents, Nanobodies, Aptamers, and so on.

Next the cells in the pool are sorted based on the detection of at least one of the one or more detectable probe(s). The comparison of a negative and positive population (i.e. one having the trait and one not having the trait lead to the identification of regulators. Sorting of cells is a technique well-known to the skilled person, and any method known in the art may be used. Non-limiting examples include Flow cytometry, including Fluorescent Activated Cell Sorting (FACS). Flow cytometry and cell sorting are well-established technologies in clinical diagnostics and biomedical research. In general, in FACS heterogeneous mixtures of cells are placed in suspension and passed across one or more laser interrogation points. Signals emitted from the particles are collected and correlated to a given phenotype such as cell morphology, surface and intracellular protein expression, gene expression, and cellular physiology. Based on user-defined parameters, individual cells can then be diverted from the fluid stream and collected into homogeneous fractions at exceptionally high speeds and a purity that approaches 100% (see Ibrahim SF Adv Biochem Eng Biotechnol. 2007; 106:19-39). As will be understood by the skilled person, the cells sorted in the method according to the invention are not viable anymore as the consequence of the fixation and permeabilization step.

Other suitable techniques include Magnetic Cell Sorting (MACS), affinity binding techniques and methods based on microfluidics (reviewed by Autebert J. Methods. 2012 57(3): 297-307). The sorting may be done is one step, or may consist of more than one step (i.e. wherein in a next step a first set of sorted cells are further sorted). The sorting results in one or more population of cells that is based on the phenotype under study. For example, the sorting may results in a first population of cells having the trait detected by the probe and a second population of cells not having the trait. The cell may also be sorted into several different populations, for example, cells that, based on the detection by the probe, does not comprise a certain protein or RNA, cells that comprise low level (user defined) of the certain protein or RNA, cells that comprise normal level (user defined) of the certain protein or RNA, and cells that comprise high level (user defined) of the certain protein or RNA. The sorting may also result in just one population, wherein, for example, all cells manifest the given phenotype (based on the probe used to detect) or all cells do not manifest the given phenotype. The one population may for example be compared to previous information obtained from a population of cells not having the phenotype/trait, or by comparison to (part of) the whole population of cells before sorting (i.e. the unsorted population).

After sorting the cell, optionally but preferably after crosslinking-based fixation, the cells may be de-cross-linked in order to make the DNA and/or RNA available for the sequencing step of the method according to the invention. Additionally, for example, when an alcohol is used for fixation and permeabilization of the cells, the cells may be further treated with a protease in order to purify the DNA/RNA from the sorted cells. In methods that do not include cross-linking, the DNA/RNA can be readily isolated using methods known to the skilled person, without the need of de-crosslinking. Cells that were fixed and permeabilized with other reagents such as formaldehyde (and, for example, a detergent) can be de-cross-linked before DNA isolation. Method for de-crosslinking the cells are readily available to the skilled person and, in part, depend on the method of fixation and permeabilization used. For example, to facilitate de-crosslinking of pellets of sorted cells, the cells may be resuspended in a buffer and incubated for several hours with agitation and after the addition of Proteinase K and lysis buffer (see Examples herein below). Other de-crosslinking protocols include incubation at 65 degrees Celsius for 5 hours, without Proteinase K, after which proteinase K is added and incubated for several hours at 42 degrees Celsius.

Thus in a preferred embodiment of the invention, the fixation of the pool of cells is a fixation that is either reversible, i.e. the method comprises a reversible fixation step with a fixation agent (see for example also Eltoum I Advanced concepts in fixation: 1. Effects of fixation on immunohistochemistry, reversibility of fixation and recovery of proteins, nucleic acids, and other molecules from fixed and processed tissues. 2. Developmental methods of fixation. J Histotechnol 2001; 24; 201-210), and/or is a method that does not affect genetic material for follow-up processing. Such methods are generally known in the art and one non-limiting example is reversible fixation with formaldehyde; an example of which in shown the Examples herein. Alternatively, as already discussed herein, fixation and permeabilization may be performed without crosslinking, for example using alcohols. In such methods, de-crosslinking is not required, and the DNA/RNA can readily be obtained.

In a next step, at least part of the cells of at least part the obtained populations are sequenced to identify one or more genetic elements (RNA or DNA) that affect the phenotype of the cells. For the current invention the method of sequencing is not critical, however preferably sequencing comprises high-throughput sequencing methods and/or next-generation sequencing technologies, for example 454 pyrosequencing, Illumina (Solexa) sequencing (see the Example herein below), SOLiD sequencing, DNA nanoball sequencing, RNA sequencing, or any other technique. Preferably the sequencing involves deep sequencing (i.e. sequencing wherein the total number of reads is many times larger than the length of the sequence under study; i.e. a depth/coverage of at least 2, 7 10 or even 50 or 100 or more).

Prior to the sequencing of the genetic material the genetic material may undergo additional preparation or processing steps, such as amplification of (part of) the genetic material using for example polymerase chain reaction (PCR). For example, when the pool of cells is treated with a mutagenesis protocol using gene trap vectors, introducing insertional mutations across the mammalian genome, the insertion sites may, prior to sequencing be amplified using PCR, for example, and preferably, using a Linear AMplificaction polymerase chain reaction (LAM-PCR) using the total genomic DNA. The skilled person is well aware of such methods, including variations thereof (see, for example, Ranzani et al. (2013) Protocol Exchange (2013) doi: 10.1038/protex.2013.009 or Schmidt et al. (2007) Nature methods 4, 1051-7).

In one embodiment total DNA or RNA is sequenced, in another embodiment only part of the DNA of RNA is sequenced.

Based on the results of the sequencing one or more genetic elements that affect(s) the phenotype may be identified, for example by comparison of the results of a first population that was sorted to manifest the given phenotype and a second (or more) population that was sorted to not manifest the given phenotype (or to a lesser extent). Differences in the DNA sequences obtained are indicative of genetic elements that are or are not involved in the given phenotype. For example, if a gene trap vector is found to be inserted in a given gene in the population of cells displaying the phenotype and not in the population of cells not showing the phenotype, such gene is considered a genetic element that affects the phenotype (as the gene trap vector inactivates the gene).

For example, a variety of methods can be used to identify genes/genetic elements into which a gene trap vector has inserted. For example, inverse PCR may be used to identify genomic sequences flanking the insertion. Alternatively splinkerette PCR is used (Horn, C, et al, Nat. Genet., 39: 807-8, 2007) or 5'-RACE (rapid amplification of cDNA ends) is used to amplify cellular sequences contained in a gene-trap fusion transcript (see, e.g., Nature Methods, 2(8), 2005). As will be understood by the skilled person, the more frequent a certain genetic element is specifically found/identified in the population of cells manifesting the given phenotype (and not or less in a population not showing the given phenotype) or the derivations of a particular genetic element are identified (e.g. collection of different mutations affecting the same gene), the more likely the candidate genetic element affects the phenotype. For example when insertional mutagenesis is used in step (a) of the method, the ratio of insertions in the genome between the sorted populations may be determined for various positions in the genome. If a genetic element is a positive regulator of a given phenotype/trait, it will show relatively less insertions in the genetic element as compared to non-relevant genetic elements in a cell population that is positive for the trait. A negative regulator of a given phenotype/trait will show relatively more insertions in a cell population that is positive for the trait. Methods for comparing the populations are well-known to the skilled person (see for example, van Opijnen et al. Nature Methods 6, 767-772 (2009) or Sun et al. Cell Reports 7, 86-93, 2014 (http://dx.doi.org/10.1016/j.celrep.2014.02.045.) Other of such possible methods are described in the Examples.

Obviously, results obtained from sequencing the cells manifesting the phenotype (or, independently, not manifesting the phenotype) may be compared to results of earlier analysis instead to comparing to a second obtained population.

In one embodiment of the invention the results obtained from the cells not manifesting the given phenotype may be used to exclude candidate genetic elements from being involved in affecting a given phenotype.

It is preferred that in step (d) at least two population of cells are obtained with the sorting of the cells based on the detection of at least one of the one or more detectable probes(s) and that in step (f) at least two population of cells are sequenced and compared to identify genetic elements that affects the phenotype of the cell.

The invention is not limited to one or two populations in step (d) of the method according to the invention; depending on the phenotype, the method according to the invention may also comprise the use of three, four, five or even more populations. By, for example comparing more populations the method may, for example, allow for the identification of genetic elements that play different roles in different populations. For example, when comparing four populations of cells having different abundance of a given mRNA (no, low, normal, high) it may be revealed that in the second population a certain genetic element A is involved, that in the third population, next to genetic element A a certain genetic element B is also involved, whereas in the fourth population only genetic element C is involved. Thus, in a preferred embodiment of the method of the invention, in step (d) at least three, four, five, six of more populations are obtained, and preferably in step (f) at least two, three, four, five, six of more populations are subjected to sequencing.

As discussed above, the genetic element may be any kind of element present in the cell. However, preferably the genetic element is a functional unit in the genetic material, preferably selected from the group consisting of a gene, an intron, an exon, a promoter and a noncoding RNA. Others include operons, operators, a transcription start site, enhancers, silencers, insulators and the like. Most preferably the genetic element that is identified is a gene.

The method disclosed herein can be employed using any kind of cell that can be subjected to the different treatments in the steps of the invention (mutagenesis fixation and so on), for example prokaryotic and eukaryotic cells. However in a preferred embodiment the cells in the pool of cells is selected from the group consisting of an eukaryotic cell, an animal cell, a plant cell, a yeast cell, a mammalian cell, a human cell, or a stem cell. The cell may, for example, be a pluripotent stem cell or an induced pluripotent stem cell. The cell may be obtained from a non-human embryo. In a preferred embodiment the cell is not obtained from a human embryo, in particular that leads to the destruction of the embryo. The method is not used for modifying the germ line identity of human beings. The cells may be primary cells or may be cell lines. The cell lines may be genetically modified or not.

The cells may have the ploidy (number of sets of chromosomes in a cell) that is normal for the organism from which the cells were originally obtained (e.g. diploid for humans and most animal). The cells may be diploid cells or, for example in the case of plant material, may be polyploid cells, for example triploid, tetraploid, pentaploid and so on. In a preferred embodiment, the cells are near-haploid cells or fully haploid cells, preferably near-haploid or fully haploid mammalian cells, more preferably a near-haploid cells or fully haploid human cells.

In almost all mammals, including humans, most somatic cells are normally diploid, i.e., they contain two homologous copies of each chromosome (other than the two sex chromosomes, which can be either homologous or non-homologous depending on the sex and particular species). The members of a homologous pair are non-identical chromosomes that both contain the same genes at the same loci but possibly have different alleles (i.e., different genetic variants) of those genes.

In contrast, a haploid cell contains only a single copy of each chromosome. A near-haploid mammalian cell, as used in the art, refers to a mammalian cell in which no more than 5 chromosomes are present in two or more copies. In some embodiments a near-haploid mammalian cell has no more than 1, 2, 3, or 4 chromosomes present in two or more copies. When none of the chromosomes are present in two or more copies, the cells are considered haploid cells.

In some embodiments of the invention the near-haploid mammalian cell is a human cell. In some embodiments of the invention the near-haploid mammalian cell is a non-human mammalian cell, e.g., a non-human primate cell or a rodent cell, e.g., a mouse, rat, or rabbit cell. In some embodiments of the invention the near-haploid mammalian cell is a hematopoietic lineage cell, e.g., a lymphoid or myeloid cell. In some embodiments of the invention the near-haploid mammalian cell is a tumor cell, e.g., a descendant of a cell that was originally obtained from a tumor. For example, the near-haploid mammalian cell is a cell of the KBM7 cell line, or a subclone thereof. In other embodiments of the invention the near-haploid mammalian cell is a leiomyosarcoma cell (Dal Sin, P., et al., J Pathol., 185(1): 112-5, 1988). Near-haploid cells are known in the art and are for example described in EP2451982.

Various method of mutagenesis may be used in the method according to the invention. Since the purpose of the method of the invention is to identity genetic elements that affect a given phenotype (forward genetics), preferably the method used for mutagenesis introduces modifications throughout the genome present in the pool of cells. In a preferred embodiment the mutations are introduced randomly or semi-randomly. Within the context of the current invention, random and semi-random mutagenesis relates to mutagenesis methods that introduce mutations in a random or semi-random manner (for example targeting certain regions present throughout the genome and based on homology). Chemical mutagens like Ethyl methanesulfonate (EMS), Nitrous acid, Mitomycin C, N-methyl-N-nitrosourea (MNU), diepoxybutane (DEB), 1, 2, 7, 8-diepoxyoctane (DEO), methyl methane sulfonate (MMS), N-methyl-N'-nitro-N-nitrosoguanidine (MNNG), 4-nitroquinoline 1-oxide (4-NQO), 2-methyloxy-6-chloro-9(3-[ethyl-2-chloroethyl]-aminopropylamino)-acridinedihydrochloride (ICR-170), 2-amino purine (2AP), and hydroxylamine (HA) are considered to cause random mutations in the genome. Also the use of radiation, e.g. ultraviolet radiation and/or radioactive radiation introduce random mutations. Alternatively, insertional mutagenesis (e.g. using retroviruses or transposons), signature-tagging mutagenesis, gene trapping, and other non-(specific) gene targeting may be used.

Alternative a mutagenesis method may be used that utilizes a library of mutagens targeting many different sites in the genetic material of the cells in the pool, but wherein each member in the library is specific for only one or a few sites in the genetic material. For example, such library may consist of a CRISPR library of guide RNA sequences, wherein each guide RNA targets a limited amount of sequences/positions in the genome of the cell in the pool, but wherein the library consists of different guide RNA's each targeting a specific sequence in the cells (which sequence may however be present more than once in the cell).

Mutagenesis may also comprise the use of the clustered regularly interspaced short palindromic repeats (CRISPR) technologies, or meganucleases including Transcription activator-like effector nucleases (TALENS), Zinc Finger Nucleases and the like. These techniques for introducing mutations are all well-known to the skilled person.

The mutagenesis treatment may, for example, be a method that at average introduces only a few mutations per cell (for example 1, 2, 3, 4, 5, . . . 10 mutations per cell on average) or more.

In a preferred embodiment the mutagenesis treatment is a random mutagenesis treatment.

In a preferred embodiment the mutagenesis involves the use of radiation, ultraviolet and ionizing radiation, mutagenic chemicals, preferably ethyl methanesulfonate, nitrous acid, or ethyl nitrosourea, insertion mutagenesis, preferably transposon-based insertional mutagenesis or retrovirus-based random insertional mutagenesis, a CRISPR library of guide RNA sequences (aimed to generate mutations into many or all human genes, promoters, enhancers or non-coding RNAs and the like), meganuclease and/or by methods that repress DNA repair (thereby accumulating mutations).

In a preferred embodiment, the cells are exposed to a particular stress condition or growth condition of interest and/or the cells are treated with a compound, preferably a drug before the cells are fixed and permeabilized in step (b), preferably between performing step (a) and step (b).

In this embodiment, the cells present in the pool may be exposed to a stress condition or growth condition or a treated with a compound, preferably a drug before the cells are fixed and permeabilized. The exposure or treatment may be prior to the treatment in step (a), during the treatment in step (a), and/or after the treatment in step (a); but before the fixation and permeabilization in step (b). The stress condition of growth conditions may be a stress of growth condition that requires the cell to adapt a given phenotype or to induce such phenotype. Alternatively such condition may be used, in combination with the treatment of step (a) to select for those cells that have adopted a phenotype (due to the treatment in step (a) that allowed the cells to better survive the stress of growth condition, and, using the method of the invention, to identify the genetic elements that affect this phenotype. For example, the stress condition may be increased temperature or salt concentration or the presence of toxic material in the growth medium. Other examples include metabolic stress, hypoxia, and exposure to pathogens.

It is to note that in the method according to the invention the pool of cells may also be a pool of cells that have been modified to already carry a mutation that in already known to cause a particular phenotype, for example a (heritable) (human) disease. When such cells are used as the pool of cells in the method according to the invention, and subjected to the various steps (a)-(f), genetic elements may be identified that, for example, in the given genetic background, affect such phenotype and may be interesting target for intervention (see FIG. 16). Thus in a preferred embodiment, the pool of cells to be used in the method of the invention comprises cells that comprise at least one mutation that causes (in the animal/human/plant, preferably human) a condition, for example an inheritable conditions. For example the condition may include diseases, including cancer, or, for example resistance to certain drugs.

Different pool of cells treated differently, e.g. subjected to different forms of stress or compounds (before, after or at the same time as the mutagenesis of gene expression modifying treatment is performed), may also be used and compared in the method according to the invention.

The method according to the invention can also be used to study the response of cells to a drug, and what genetic elements are involved in a given phenotype related to the response to a drug (for example, drugs that induce stress-pathways or induce phosphorylation of proteins) For example, a given drug may be known to cause inhibition of phosphorylation of a certain protein. By exposing the cells to the drug and performing the method according to the invention, genetic elements may be identified that, for example, are involved in overcoming the inhibition of phosphorylation of said protein, or that are involved in the inhibition.

With the method according to the invention, in some embodiments, the same pool of cells is subjected to a mutagenesis treatment. The mutagenesis treatment is a treatment that causes many different mutations (random or targeted) in one and the same pool of cells. In other words, a pool of cells is obtained wherein individual cells comprise different mutations, not only in number, but also with respect to the location of the mutation. The method according to the invention makes it possible to identify from this heterogeneous pools of cells, these cells manifesting the phenotype of interest, and in turn the genetic element(s) that is (are) responsible for affecting (or causing) the trait (or phenotype).

In a preferred embodiment of the invention, the fixation reagent to fix the cells is selected from the group consisting of crosslinking reagents, preferably formaldehyde, paraformaldehyde, formalin and glutaraldehyde or non-crosslinking reagents, preferably mercuric chloride-based fixatives, ethanol, methanol or acetone.

The fixation reagent used in the method according to the invention may be any type of suitable fixation reagent as long as it allows that genomic DNA/RNA can subsequently solubilized and used for sequence analysis (which may or may not involve a further DNA amplification step). However, preferred materials included crosslinking reagents, preferably formaldehyde, paraformaldehyde, formalin and glutaraldehyde or non-crosslinking reagents, preferably mercuric chloride-based fixatives, ethanol, methanol or acetone.

Preferably the permeabilization reagent is selected from the group consisting of solvents, preferably methanol and acetone, or detergents, preferably saponin, digitonin, Triton X-100 and Tween-20. Within the context of the current invention, the skilled person is well aware of suitable methods for fixating and permeabilizing the pool of cells.

The detectable probe may be any type of probe that may be used to detect the phenotype or an element thereof. Preferably the detectable probe binds to a protein, a post-translation modified protein, a lipid, DNA, RNA, or binds or detects a metabolite or cellular element. In other words, any probe that can be detected and that can be used to detect RNA, proteins, protein modifications (e.g. modified by ubiquitin, methyl groups, lipids, and so on), RNA modifications, DNA modifications or any metabolite can suitable be used in the method of the invention.

For example, and in a preferred embodiment, the probe is an antibody, preferable a labeled antibody, preferably with a fluorescent label, or an antibody that can be detected with a further antibody comprising such label. The antibody may also be a phosphospecific antibody (e.g. an antibody that only binds to a phosphorylated version of the protein). The detectable probe may also be a receptor for a ligand, or a ligand for a receptor. The detectable probe may also be a nucleic acid that will specifically hybridize based on sequence complementarity with a target (DNA or RNA) in the cell. Other useful probes, including antibody mimetics, as described above, can also be employed.

The term cellular element in this context refers to any other element in the cell not being a genetic element and includes but is not limited to the proteins, lipids and sugars and carbohydrates present in the cell, but also included metabolites and biomolecules present in the cell, organelle or membranes.

Any suitable method of sorting the cells may be utilized in the method of the invention, as long as it may be used to detect a probe used in the method of the invention. In a preferred embodiment sorting involves flow cytometry, FACS analysis, mass cytometry, and/or magnetic sorting.

Preferably, the probe used in the method of the invention comprises a detectable moiety, preferably selected from a fluorescent moiety, a radioactive moiety, magnetic moiety, or label that can be measured using mass-spectrometry. Such labels and the use thereof are well-known to the skilled person.

In a preferred embodiment of the method according to the invention, the method is used for a phenotype that is manifested in the cytosol, inside an organelle, in the membrane of an organelle or in the cell membrane, preferably on the inner layer of the cell membrane.

Preferably the phenotype is a phenotype that requires permeabilization of the cells in order to allow detecting of the phenotype with the probe.

The method of the invention may be used for any type of phenotype. Preferably the phenotype is or involves increased protein abundance, decreased protein abundance, increased protein activity, decreased protein activity, increased post-translational modification of a protein, decreased post-translational expression of a protein, increased mRNA abundance or decreased mRNA abundance.

In another aspect there is provided for a method for identifying a modulator, for example an inhibitor or activator, of an (endogenous) gene product encoded by a candidate gene that affects a phenotype of a cell, preferably wherein said phenotype is manifested (or detected and present) intracellularly, the method comprising the steps of:
(a) Subjecting a pool of cells to mutagenesis treatment;
(b) Fixating of the pool of cells, preferably with a fixation reagent, and optionally a cross-linking agent, and permeabilizing the pool of cells, preferably with a permeabilization reagent;
(c) Treating the pool of cells with one or more detectable probe(s), preferably an antibody or a (fluorescent) RNA probe, to detect the affected (or manifested) phenotype;

(d) Sorting the cells based on the detection of at least one of the one or more detectable probe(s) to obtain one or more population of cells,
(e) Optionally, de-crosslinking the cells in each of the obtained populations of cells;
(f) Sequencing at least part of the cells of at least part of the obtained populations of cells to identify a genetic element that affects the phenotype of the cell, wherein the genetic element is a candidate gene.
(g) Identifying a modulator that affects expression or activity of an expression product of said identified candidate gene that affects the phenotype of the cell.

With the method according to the invention genetic elements may be identified that affect a given phenotype. Based on the genetic element, a corresponding cellular element can be recognized, for example, a protein which activity, expression or abundance is modulated by the identified genetic element (for example the genetic element is the gene encoding the protein). In turn, a modulator of the activity of the gene product (for example protein) of the identified candidate gene may be identified using screening assays. The modulator may for example directly influence expression of the gene product or may modulate the activity of the protein or may modulate breakdown or post-translational processing of the protein.

The methods described herein may be used for various purposes. Preferably the methods are used for establishing or analyzing biological pathways, for identifying genes involved in disease, preferably in cancer, for studying drug-target interactions, for studying drug-drug interactions, or to analyze suppression or modulation of a phenotype, preferably wherein the phenotype is a phenotype associated with a disease. In view of the disclosure herein, the skilled person understands how the method according to the invention may be used for the above given purposes.

The modulator may be any kind of compound, including organic or inorganic compounds, candidate drugs, and the like.

It is clear for the skilled person that the method according to the invention does not only allow for the identification of a genetic element, but that the method consequently also allows for the identification of cellular elements that are related to or correspond to the genetic element. For example, based on the identified genetic element, the corresponding protein or enzyme, or related genetic element (e.g. promoter and gene) or even pathway comprising more than one protein, may be identified.

Figure 16:
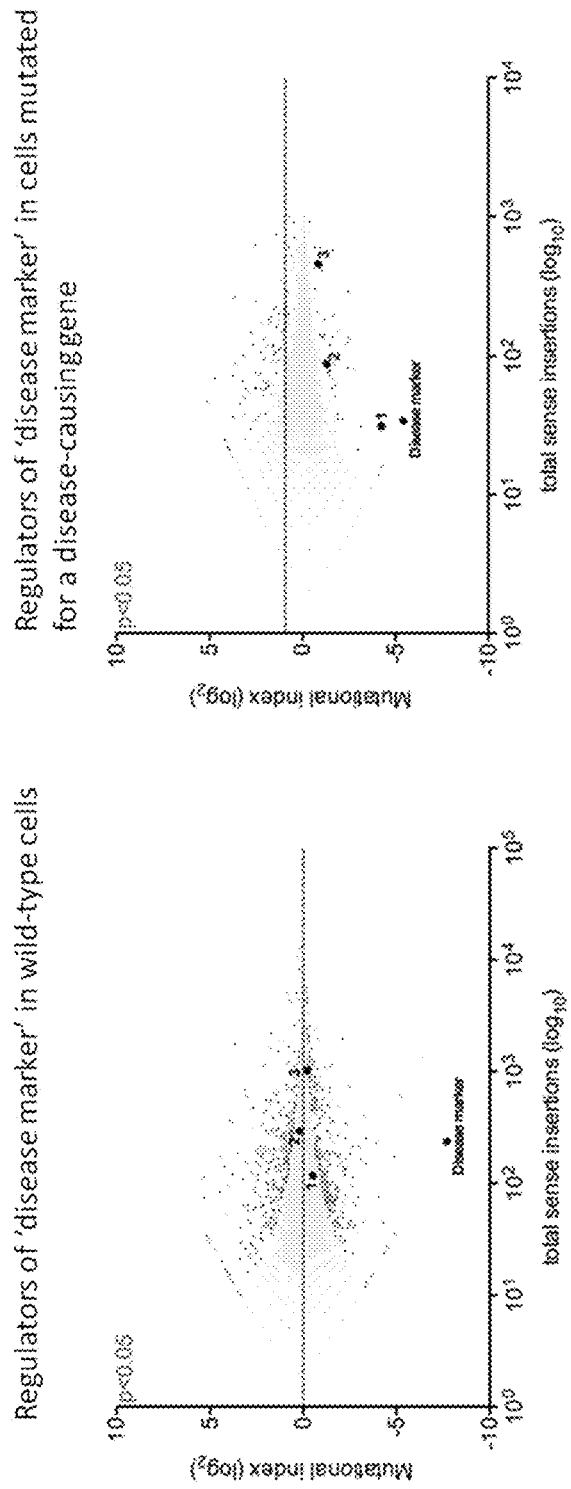
FIG. 16. Haploid genetic screens identify genes that upon mutation alter the levels of a disease marker in cells carrying a disease-inducing mutation but not in wild-type cells.

The method of the invention shows many advantages over those in the art and allows the identification of genetic elements that could not be identified by the prior art methods, as is exemplified herein, including for example the identification of targets for disease suppression (see FIG. 16). One of the advantages of this approach is that the method directly couples phenotypes (or quantitative biomolecule measurements) to actual mutations in the genome and allows doing so using millions of cells that have millions of different genotypes. The method allows to do so in cells that are fixated and that can no longer be grown to increase the number of mutant genomes, thereby allowing analysis of phenotypes that are, for example, present intracellulary. In one embodiment this is achieved by using e.g. gene traps or comparable insertion mutagenesis based approaches. When for example a gene trap is used, integrations occur across the entire genome and one cannot design 2 specific primer sequences to recover the affected flanking DNA sequences. This can however be achieved with the method that was developed where an optimized LAM-PCR protocol was developed that enables the recovery of gene-trap insertion sites from very few cells and even from an individual cells that were fixed and permeabilized. Steps in making the recovery sensitive enough is, for example, the use of a double-biotinylated capture primer, Accuprime polymerase a recombinant RNA ligase that can also ligate single-stranded DNA and the use of a sequence-optimized pre-adenylated linker. This approach works very well with such gene traps and comparable insertion mutagenesis method. For example this approach also works by making use of a pooled CRISPR library for mutagenesis, but the use of gene traps is preferred. Directly coupling mutations in the genome to phenotypes increases the accuracy (see below) as well as the strength of the signal.

An additional advantage of the method of the invention is that for many genes several hundred or thousand mutations can be measured per individual gene. Because of this, one can count the frequency of mutations in individual genes. Because counting can be used, one does not need to measure the abundance of each mutation (or gene-perturbing agent such as shRNA or CRISPR). Measuring the abundance of each component of a complex library is challenging on a limited amount of biological material due to variations that are introduced by PCR amplification. In the developed method, the frequency with which a mutation is recovered is ignored but the number of mutations in individual genes are counted and compared. When different phenotypic states are now compared (e.g. cells with a high amount of LAMP1 protein versus cells with a low amount of LAMP1 protein), this again results in the identification of genes that affect the phenotypes with very low false positive results.

The quantitative nature of this mutation spectrum and the fact that the majority of the hits are not caused by noise make it possible to compare mutation spectrums to the intensity of a phenotype (high/low biomolecule), across different phenotypes (e.g. genes required for the biogeneration of an acetylated or tri-methylated lysine residue) or across genotypes (genotype-specific suppressors or enhancers of a phenotype). Last, by comparing many different phenotype read-outs, genes can be clustered based on their phenotypic output. Thus, comparative analysis of mutation spectrums facilitates new ways to study and compare biological phenotypes. Importantly, this would not be practical when an approach is used that reports a significant amount of noise or that requires significant experimental follow-up to separate the real hits from the noise.

Finally, because the mutation spectra can be compared directly, a comparative screen in wild-type and mutant cells can point out genotype-specific phenotype enhancers or suppressors. Importantly, when the genotype of interest is related to human disease (for example a heritable disease or disease caused by somatic DNA mutations), this can point out targets for disease suppression. This can be used to identify gene products that—when inhibited-protect against disease. Drugs developed to act on such targets could be used to suppress disease (see FIG. 16). Having fully described this invention herein, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein.

It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Methods

Gene-trap retrovirus required for the mutagenesis of HAP1 cells (for example described in Carette et al. (2011). Nature, 477(7364), 340-3. doi:10.1038/nature10348; available from www.horizon-genomics.com/hap1-wildtype.html) was produced in HEK293T cells using the gene trap vector described previously (Jae et al., Science 2013 340(6131): 479-83) and a similar gene-trap retrovirus was used in which green fluorescent protein (GFP) was exchanged for blue fluorescent protein (BFP).

Cells were seeded in 12 T175 flasks at 40% confluence. The next day the medium was replaced with DMEM supplemented with 30% fetal calf serum (FCS) prior to transfection with 6.6 microgram gene trap plasmid per T175 flask, in combination with the packaging plasmids Gag-pol, VSVg and pAdv (Carette et al., Science 2009 326(5957):1231-1235). The medium was harvested 48 hours post transfection and subsequently concentrated by ultracentrifugation at 21.000 rpm for 2 hours at 4° C. The supernatant was discarded and the pellets were resuspended in 200 microliter phosphate buffered saline (PBS, Life technologies) overnight at 4° C. Retrovirus-containing medium was collected and concentrated twice daily for three days.

To generate a mutagenized HAP1 cell population, 40 million HAP1 cells were seeded and transduced with gene-trap retrovirus from two combined harvests on three consecutive days in the presence of 8 microgram/ml protamine sulfate (Sigma). The mutant library was subsequently expanded for a maximum period of 10 days prior to analysis of an intracellular phenotype via FACS staining.

For genetic screens, mutagenized HAP1 libraries were expanded to $3 \times 10^9$ cells, dissociated using trypsin-EDTA (Life technologies) and subsequently fixed using BD fix buffer I (BD biosciences) for 10 minutes at 37° C. Following a wash with PBS containing 1% FCS, cells were permeabilized by suspension in cold (-20° C.) BD permeabilization buffer (BD biosciences) while vortexing and incubated on ice for 30 minutes.

After washing twice in PBS/1% FCS, cells were filtered through a 40 micrometer strainer (BD Falcon™). Staining was performed in 100 microliter per $10^7$ cells with specific primary antibodies (1:200-1:400) for 1 hour at room temperature. Cells were washed in washing buffer (PBS/1% FCS) twice and stained with the secondary antibody (ALEXA488, -568 or -647 antibody, Life Technologies) for one hour in the dark.

Additionally, in order to minimize potential confounding effects of diploid cells which are heterozygous for alleles carrying gene-trap integrations, deoxyribonucleic acid (DNA) content was stained using either 3 microM 4',6-diamidino-2-phenylindole (DAPI) or 10 microgram/ml propidium iodide (Life Technologies) solution. In the latter case cells were also treated with 100 microgram/ml RNAse A (Qiagen) at room temperature for 1 hour.

For antibody staining in the nuclear compartment (e.g. histone modifications), cells were fixed in the dark with Fixation/Permeabilization buffer (eBioscience) for one hour at room temperature. After washing two times in Permeabilization buffer containing 5% FCS, cells were resuspended in 2 M HCl and incubated 30 min at room temperature to aggregate cells and denature DNA. Thereby, cell suspension was gently mixed. For neutralization, cells were washed with 0.1 M Na2B4O7 (pH=8.5) and stained with the primary antibody (100 microliter per $10^7$ cells; 1:200-1:400) in Permeabilization buffer containing 5% FCS (eBioscience). After one hour at room temperature, cells were washed and stained with secondary antibody for one hour at room-temperature in the dark (in permeabilization buffer containing 5% FCS (eBioscience)). The last washing steps were performed in PBS/1% FCS.

Following staining, cells were sorted on either a Biorad S3 Cell sorter (combination: BFP gene trap, Alexa488 secondary antibody, PI to measure DNA content) or an Astrios Moflo (combination: GFP gene trap, Alexa488, -568 or -647 antibody, DAPI to measure DNA content) based on the signal of interest (approximately 1-5% highest and lowest staining populations for query antibody) and DNA content (1n).

Sorted cells were pelleted by centrifugation (2500 rpm 10 min.) and genomic DNA was isolated using Qiagen DNA mini kit. To facilitate de-crosslinking pellets were resuspended in PBS (200 microliter/10 million cells) and after the addition of Proteinase K (Qiagen) and lysis buffer (buffer AL, Qiagen) incubated overnight at 56° C. with agitation. The following day DNA was isolated according to manufacturer's specifications and measured by Nanodrop2000 spectrophotometer (Thermo fisher).

Insertion sites were amplified using a Linear AMplificaction polymerase chain reaction (LAM-PCR) using the total genomic DNA (0.5-2 microgram/reaction), with each 50 microliter reaction (rxn) containing 1 mM MgSO4, 0.75 pmol double-biotinylated primer (5'-/double biotin/ggtctc-caaatctcggtggaac-3')(SEQ ID NO: 1), Accuprime Taq HiFi (0.4 microliter/rxn) and the supplied buffer II (Life technologies). The reaction was performed in 120 cycles with an annealing temperature of 58° C. for 30 seconds and an extension temperature of 68° C. for 60 seconds. To capture biotinylated single-stranded DNA (ssDNA) products, PCR reactions were combined with M270 streptavidin-coated magnetic beads (Life technologies) in 2× binding buffer (6 M LiCI, 10 mM Tris, 1 mM EDTA, pH=7.5) for 2 hours at room temperature and subsequently captured using a magnet. Prior to binding, the beads were washed once in PBS-containing 0.1% bovine serum albumin (BSA) in 1.5 ml non-stick tubes (Life technologies). Following magnetic precipitation, beads were washed three times with PBS containing 0.05% Triton X-100 (Sigma) prior to linker ligation.

A ssDNA linker (5'/phospho/atcgtatgccgtclictgcttgactcagtagttgtgcgatggattgatg/dideoxycytidine/3') (SEQ ID NO: 2) was ligated to the 3' end of biotinylated products in N×10 ul reactions containing 2.5 mM MnCh, 1 M betaine, 12.5 pmol linker, 1 microliter and 0.5 microliter of Circligase II (Illumina) buffer and enzyme respectively, with N=number of LAM-PCR reactions. Alternatively, a pre-adenylated linker (5'/Adenyl/atcgtatgccgtcttctgcttgactcagtagttgtgcgatggattgatg/dideoxycytidine/3') (SEQ ID NO: 3) was ligated to the single stranded amplified DNA product using $E.$ $coli$-purified TS2126 thermostable RNA ligase 1 from $Thermus$ $scotoductus$ bacteriophage (Blondal et al, Nucleic Acid Research 2005, 33(1) 135-142, patent WO 2010/094040 A1) in N×10 microliter reactions containing 12.5 pmol adenylated-linker, 18.75% PEG6000, 2.5 microgram BSA, 2.5 mM MnCh, 1 microliter buffer (500 mM MOPS, 100 mM KCl, 50 mM MgCl2, 10 mM dithiothreitol (DTT)) and 2 microgram RNA ligase. All ligation reactions occurred at 60° C. for 2 hours in non-stick 1.5 ml tubes (Life technologies) and were followed by three washes with PBS with 0.05% Triton X-100 (Sigma) after 20 minutes incubation at room temperature. Subsequently, a PCR reaction was performed that introduced the adaptors sequences required for Illumina sequencing (P5 and P7) in N×50 microliter reactions containing 25 pmol of each primer, 5 microliter buffer II and 0.6 microliter Accuprime Taq HiFi (Life technologies) (with N=0.5×No. of LAM-PCR reactions).

This final amplification was carried out using 18 cycles and annealing temperature of 55° C. for 30 s followed by an extension (at 68° C.) for 105 s using primers: 5'-aatgatacggcgaccaccgagatctgatggttctctagcttgcc-3' (SEQ ID NO: 4) and 5'-caagcagaagacggcatacga-3' (SEQ ID NO: 5).

Products were purified (PCR purification kit, Qiagen) and sequenced as 51 bp single-reads (18 picomolar loading concentration) on an Illumina HiSeq2000 (Illumina) or HiSeq2500 (Illumina) using sequencing primer 5'-ctagcttgccaaacctacaggtggggtctttca-3' (SEQ ID NO: 6).

Following deep sequencing, gene-trap insertion sites were identified as reads aligning uniquely to the human genome (hg19) without or with a single mismatch using bowtie (Langmead et al., Genome Biol 2009, 10:R25) for both the high and low sorted intracellular phenotype populations. Aligned reads were intersected with hg19 gene coordinates to establish intragenic insertion sites and their orientation respective to the gene using intersectBED (Quinlan and Hall, Bioinformatics 2010, 26 (6): 841-842). For the purpose of this analysis, insertion sites integrated in sense within a gene were considered disruptive. For overlapping genes with opposite coding strands, only the unique regions were considered. In addition, for overlapping genes using the same coding strand the gene names were concatenated. In order to identify genes that are enriched for disruptive gene-trap integrations in either query population, the number of disruptive insertion sites in each gene and in total of one population (e.g. signal high) was compared to those values in the other population (e.g. signal low) using a one-sided Fisher exact test and vice versa. Resulting P-values were adjusted for multiple testing using Benjamini and Hochberg FDR correction. Fishtail plots were created by calculating the ratio of the number of disruptive integrations per gene in both populations normalized by the number of total integrations in the two populations (plotted on the y-axis) and the sum of disruptive integrations identified in both the high and low populations (plotted on the x-axis).

For genetic CRISPR/Cas9-based screens, lentiviral GeCKO libraries (version 1 and version 2) were obtained from the Zhang lab through Addgene (Shalem et al., 2014 Science, 343(6166), 84-87. doi:10.1126/science.1247005; www.addgene.org/crispr/libraries/geckov2/). The libraries were amplified in $E.$ $Coli$ and DNA was purified according to the manufacturer's instructions (QIAgen). Library complexity was confirmed by deep sequencing (>98% recovery rate). Lentivirus was produced in HEK293T cells using the appropriate packaging plasmids. Virus was harvested on multiple days and pelleted in a Beckmann SW28 rotor (21.000 rpm for 2 hours at 4° C.). Virus was resuspended in complete medium supplemented with 50 mM HEPES and frozen down in aliquots at −80° C. After virus titration, 100 million HAP1 cells were transduced with the lentiviral libraries and selected with 0.75 microgram/ml puromycin 2 days after infection. Resistant cells were expanded for 6-8 days after which cells were frozen down in aliquots of 50 million cells per vial. For a single screen, several aliquots were thawed and seeded in multiple T175 flasks. Cells were fixed and permeabilized after 7 days of culturing (aiming for $\pm1.10^9$ cells) and processed for antibody staining and sorting as described above. Deep sequencing of the sorted cell populations and data analysis was carried out as described by Shalem et al. 2014, with minor modifications. Primers used for the initial PCR to amplify the library from the isolated genomic DNA: 5'-AATGGACTATCATATGCTTACCGTAACTTGAAAGTATTTCG-3' (SEQ ID NO: 7) and 5'-CTTTAGTTTGTATGTCTGTTGCTATTATGTCTACTATTCTTCC-3' (SEQ ID NO: 8). For the second, nested PCR2 on the product of PCR1: 5'-AATGATACGGCGACCACCGAGATCTACACTCTTTCCCTACACGACGCTCTTCCGATCT NNNNNNtcttgtggaaaggacgaaacaccg-3' (SEQ ID NO: 9). and 5'-CAAGCAGAAGACGGCATACGAGATGTGACTGGAGTTCAGACGTGTGCTCTTCCGATC Ttctactattctttccctgcactgt-3' (SEQ ID NO: 10).

Generation of KCTD5 Knockout Cells

Hap1: CRISPRs were designed targeting KCTD5 (KCTD5#1 5'-caccGAGGTGCCGCCGACGTTGAGT-3' (SEQ ID NO: 11) and KCTD5#2 5'-caccGGACGTTGAGTCGGACCCACT-3') (SEQ ID NO: 12) and cloned into px330 (Cong et al. Science. 2013, PMID: 23287718). HAP1 cells were transfected with one px330 vectors in addition to a vector containing a guide RNA to the zebrafish TIA gene (5'-ggtatgtcgggaacctctcc-3') (SEQ ID NO: 13) and a cassette of a 2A sequence followed by a blasticidin resistance gene, flanked by two TIA target sites. Co-transfection with px330 results in excision of the cassette from the plasmid and subsequent sporadic incorporation at the site of the targeted genomic locus by non-homologous end joining (similar as described in Maresca et al, Genome Res. 2013 March; 23(3):539-46.). Successful integration of the cassette into the targeted gene disrupts the allele, renders cells resistant to blasticidin, and provides a tag at the location of the mutation. Four days following transfection the culture medium was supplemented with blasticidin (10 microgram/ml). Surviving colonies were clonally expanded. HEK 293T: An additional CRIPSR was designed targeting KCTD5 (KCTD5#3 5'-caccGAGGATTTCGGGTCCCG-GCAC-3') (SEQ ID NO: 14) and cloned in px330. Cells were transfected with CRISPR KCTD5#3 and CRISPR KCTD5#1 or CRISPR KCTD5#3 and CRISPR KCTD5#2, co-transfected with pMX-ires-Blast. Co-transfection of two CRISPRs will result in double stranded breaks at two positions in the gene, resulting in a deletion of the genomic region. Transfection selection was performed using blasticidin (80 microgram/ml) for 2 days. Surviving colonies were clonally expanded and genotyped.

TABLE 1 antibodies used in the various examples

| Antibody | Application | Dilution | Cat. number | Company |
|---|---|---|---|---|
| pS473 AKT | FACS, WB | 1:400 (FACS) 1:1000 (WB) | 4058 | Cell signaling Technologies |
| AKT | WB | 1:1000 (WB) | 9272 | Cell signaling Technologies |
| KCTD5 | FACS, WB | 1:400 (FACS) 1:1000 (WB) | 15553-1-AP | Proteintech Europe |
| GNB1 | WB | 1:5000 (WB) | GTX114442 | GeneTex |
| CDK4 | WB | 1:5000 (WB) | sc-260 | Santa Cruz Biotechnology |
| phospho-p38alpha | FACS, WB | 1:400 (FACS) 1:1000 (WB) | 4511 | Cell signaling Technologies |
| H3K27me3 | FACS, WB | 1:400 (FACS) 1:1000 (WB) | 39155 | Active Motif |
| gammaH2AX | FACS, WB | 1:400 (FACS) 1:1000 (WB) | 2577 | Cell signaling Technologies |
| IkappaBalpa | FACS, WB | 1:400 (FACS) 1:1000 (WB) | 4814 | Cell signaling Technologies |
| IRF1 | FACS, WB | 1:400 (FACS) 1:1000 (WB) | 8478 | Cell signaling Technologies |
| alpha-dystroglycan | FACS | 1:60 (FACS) | IIH6C4 | Merck Millipore |
| LAMP1 | FACS | 1:400 (FACS) | [H4A3] (ab25630) | Abcam |

Results and Discussion

The results of various experiments performed are shown in the figures.

FIG. 1 shows the results of a genetic screen on a mutagenized population of HAP1 cells that has been fixed with paraformaldehyde. Previously (Jae et al, Science, 2013) an antibody that recognizes glycosylated dystroglycan at the cell surface was used to enrich for mutants that lacked the respective antigen at the cell surface. Living cells were sorted, expanded in culture and subjected to deep-sequencing of the gene-trap insertion sites (FIG. 1A). In FIG. 1B (published in Jae et al, 2013), a plot showing the genes enriched for mutations in the viable selected cell population is shown. Genes required for glycosylation of alpha-dystroglycan were identified. FIG. 1C and FIG. 1D show the results with the method according to the invention. The same antibody staining was carried out as described above but now on cells fixed with paraformaldehyde. In this case, dead cells were directly subjected to de-crosslinking (by heat) and genomic DNA isolation without any prior amplification of genomes inside living cells. Recovery of the gene-trap integration sites from the fixed non-expanded cells yields a typical smear of LAM PCR amplified DNA. The gene-trap mutations were identified using deep sequencing and genes were analyzed for enrichment of disruptive mutations. These results show that fixed, non-expanded cells also are a suitable source for the identification of genes required for the glycosylation of alpha-dystroglycan. This experiment demonstrates that a screen that was carried out previously on living cells could be recapitulated on a cell population that was fixed and non-viable at the time of phenotypic examination. It demonstrates further that individual fixed mutant cells can be used as a source to recover and sequence genomic mutations (gene-trap insertions).

Figure 2A:
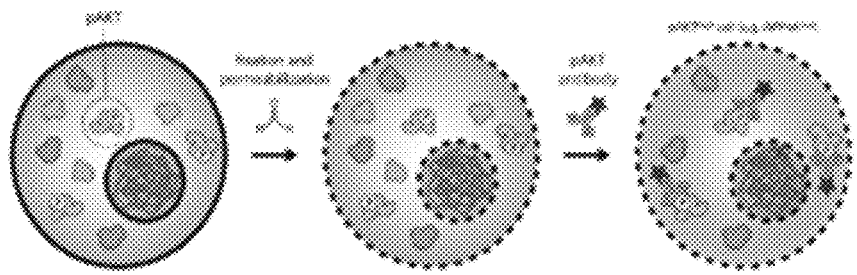
FIG. 2A. Depiction of how a haploid or near-haploid cell population that has been mutagenized using a retroviral gene-trap is fixed, permeabilized and subsequently fluorescently labeled using antibodies directed against phospho-AKT.
Figure 2B:
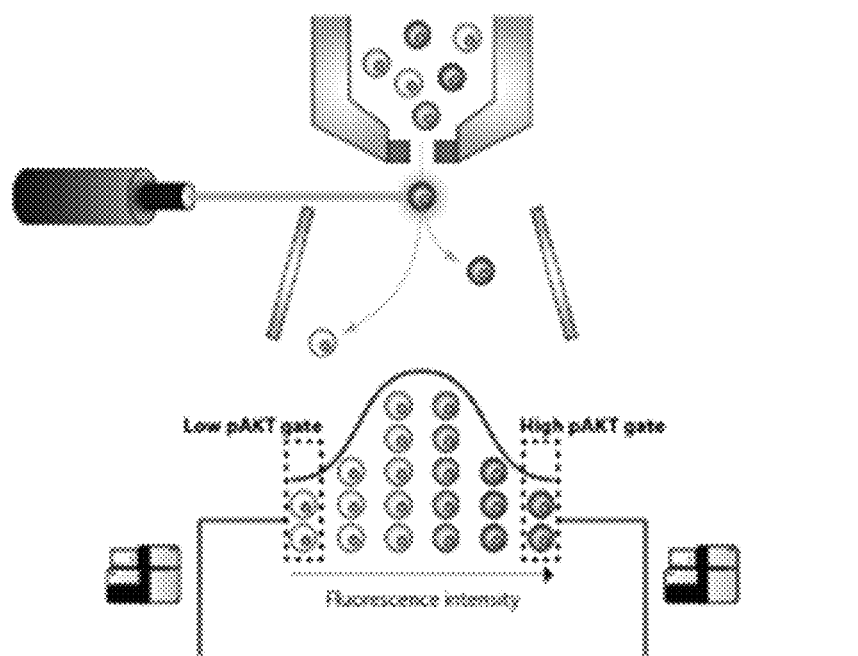
FIG. 2B. Depiction showing how cells that were fixed, permeabilized and stained for phospho-AKT are separated using flow cytometry to enrich for pools displaying high or low (highest/lowest 1-5% of total population) AKT phosphorylation. Subsequently, genomic DNA is isolated from both cell populations and used to map gene-trap insertion sites.
Figure 2C:
FIG. 2C. A plot showing the frequency of disruptive gene-trap insertions detected in a known negative regulator (INPP4A) of AKT phosphorylation in the left (low phospho-AKT) and right (high phospho-AKT) cell population. Mutants for INPP4A were enriched in the cell population with 'high' phospho-AKT signal.

FIG. 2 shows phenotypic separation of a pool of mutagenized cells and sequencing of gene-trap insertion sites. FIG. 2A is shown how a haploid or near-haploid cell population that has been mutagenized using a retroviral gene-trap is fixed, permeabilized and subsequently fluorescently labeled using antibodies directed against phospho-AKT (serine473). FIG. 2B shows how cells that were fixed, permeabilized and stained for phospho-AKT were separated using flow cytometry to enrich for pools displaying high or low (highest/lowest 1-5% of total population) AKT phosphorylation. Subsequently, genomic DNA was isolated from both cell populations and used to map gene-trap insertion sites. FIG. 2C shows a plot showing the frequency of disruptive gene-trap insertions detected in a known negative regulator (INPP4A) of AKT in the left (low phospho AKT) and right (high phospho-AKT) cell population. The plot shows that mutants for INPP4A were enriched in the cell population with 'high' phospho-AKT signal. This experiment demonstrates that, using the method according to the invention, the mutagenized cell populations that have been selected for differential AKT phosphorylation are enriched or depleted for mutations in a known regulator of the interrogated intracellular phenotype.

Figure 3A:
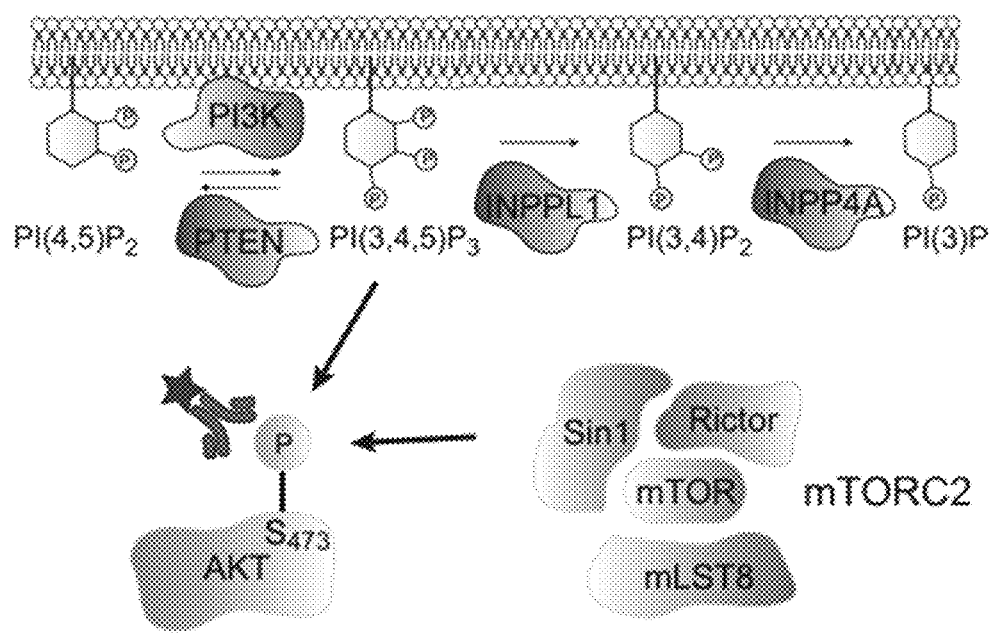
FIG. 3A. A schematic outline of the pathway leading to AKT phosphorylation involving PIP3-signaling, and the mTOR complex II (mTORCII).
Figure 3B:
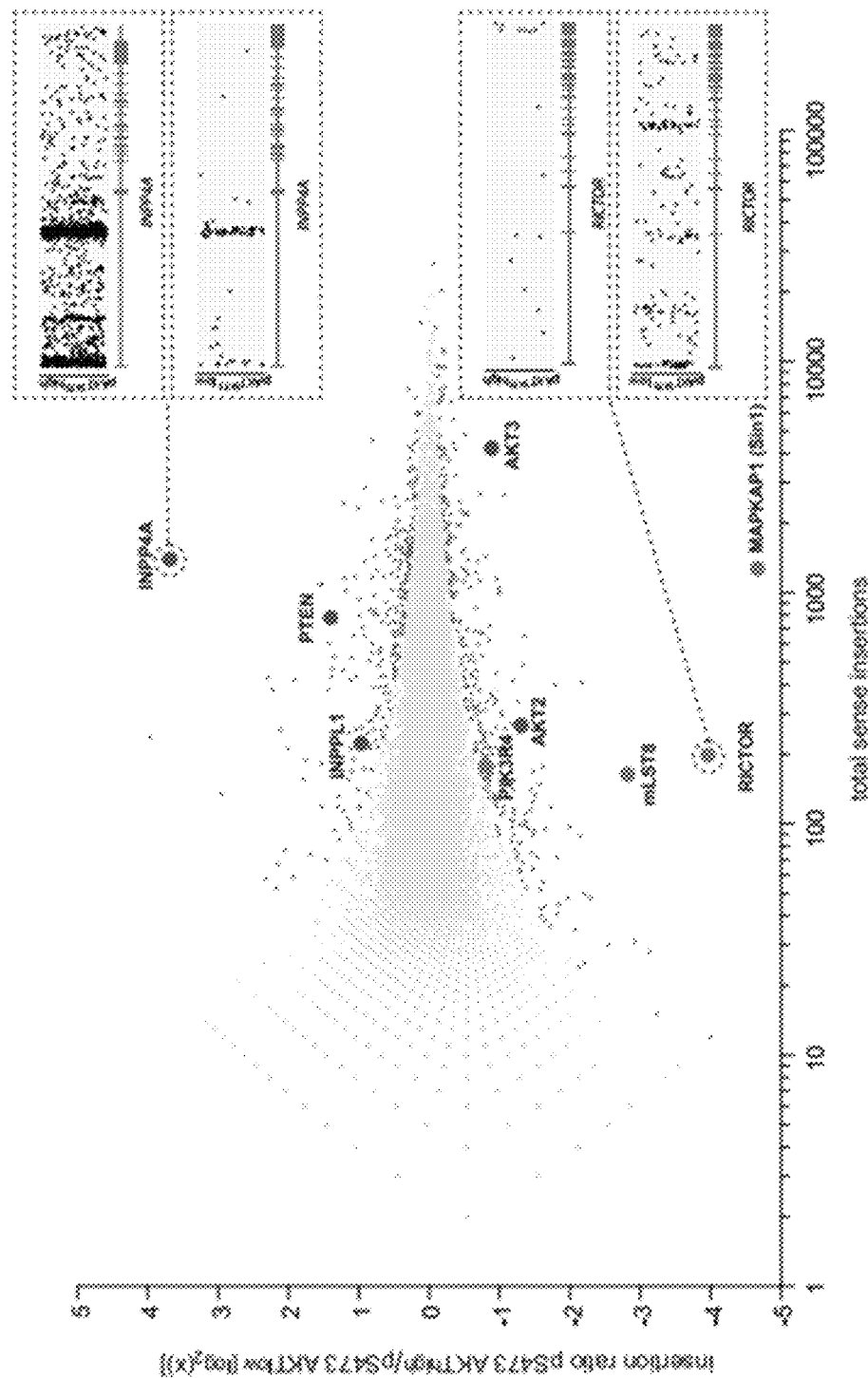
FIG. 3B. A plot showing the relative number of gene trap mutations per gene in the phospho-AKT 'high' population compared to the 'low' population. Genes that affect AKT phosphorylation when mutated show a significant change in their mutation frequency in the high versus the low population. A number of significant outliers that are known regulators of AKT signaling are labeled. Additionally, for both a positive as a negative regulator, the location of individual unique mutations is plotted on the gene.
Figure 4A:
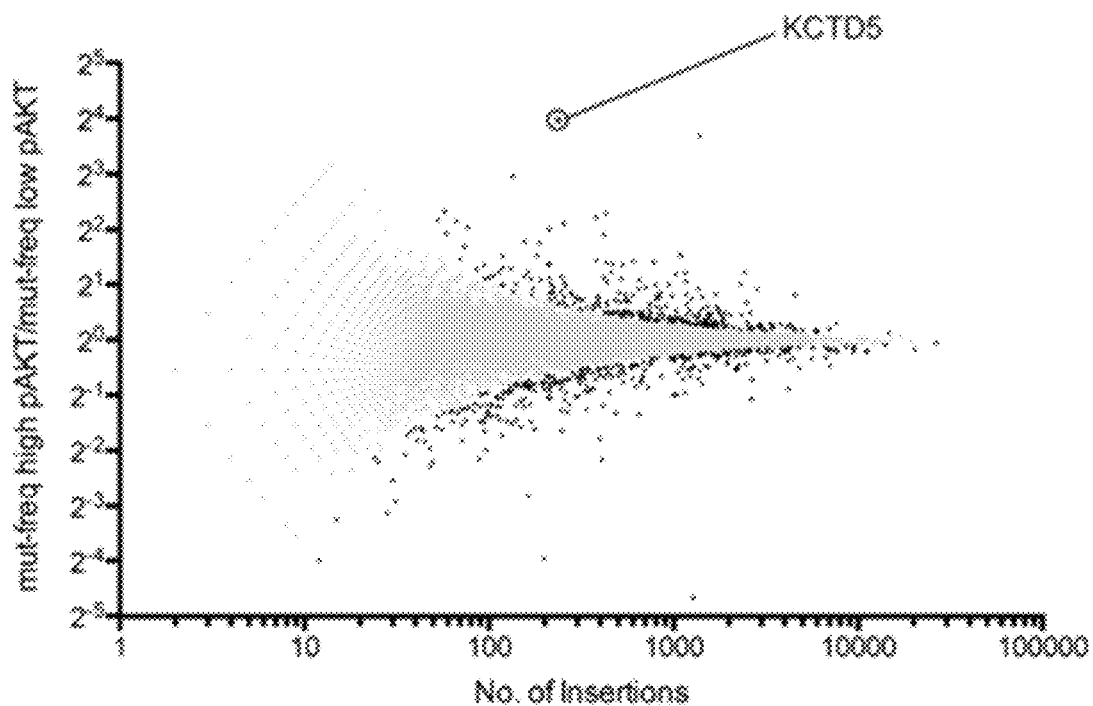
FIG. 4A. The genome-wide screen for AKT regulators identified KCTD5 as a negative regulator of AKT phosphorylation.
Figure 4B:
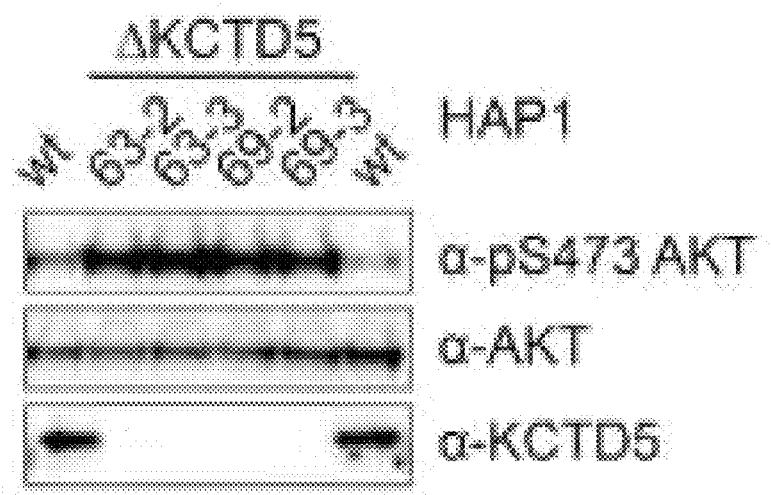
FIG. 4B. A loss-of-function mutation of KCTD5 in HAP1 cells using CRISPRs leads to an increase in AKT phosphorylation as assessed by immunoblotting.
Figure 4C:
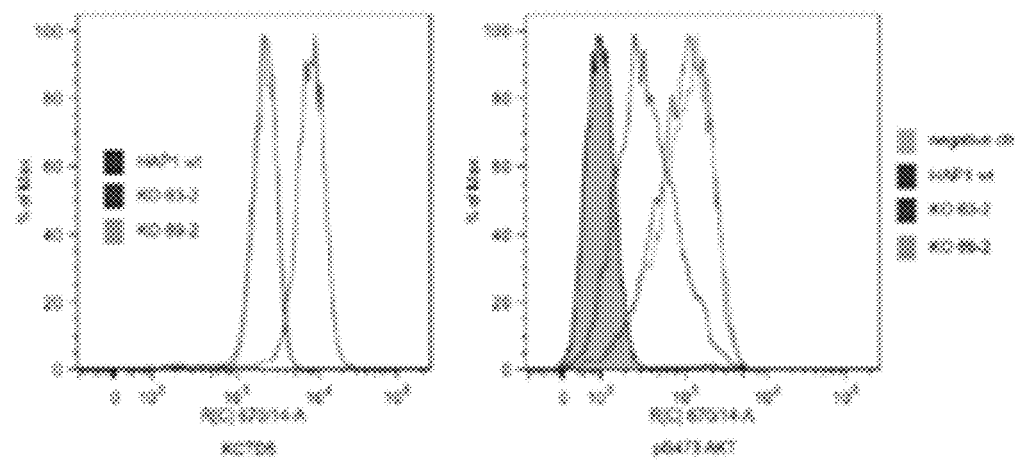
FIG. 4C. CRISPR-generated KCTD5 knockout cells show increased staining for AKT phosphorylation when examined by flow-cytometry FIG. 4D. Restoration of KCTD5 expression in the CRISPR-generated knockout cells normalizes AKT phosphorylation as assessed by immunoblotting.
Figure 4D:

FIG. 3 shows a genome-wide mutagenesis screen to identify regulators of AKT phosphorylation. FIG. 3A shows a schematic outline of the pathway leading to AKT phosphorylation involving PIP3-signaling, and the mTOR complex II (mTORCII). FIG. 3B shows a plot showing the relative number of gene trap mutations per gene in the phospho-AKT 'high' population compared to the 'low' population. Genes that do not affect AKT phosphorylation are found to be mutated with a comparable frequency in the 'high' and the 'low' populations (highest/lowest 1-5% of population). Genes that affect AKT phosphorylation when mutated show a significant change in their mutation frequency in the high population versus the low population. Known regulators of the pathway (e.g. PTEN, LST8, SIN1) are identified (both negative and positive regulators). This experiment shows that the mutation frequencies in the separate cell populations can be examined genome-wide leading to the identification of known positive and negative regulators of the AKT pathway. Importantly, numerous new factors show a significant bias in their mutation frequencies (dark grey dots) and are therefore linked to AKT phosphorylation.

FIG. 4 shows that KCTD5 affects AKT phosphorylation. FIG. 4A shows that the genome-wide screen for AKT regulators with the method according to the invention identified KCTD5 as a significant outlier. FIG. 4B shows that a loss-of-function mutation of KCTD5 in HAP1 cells using CRISPRs leads to an increase in AKT phosphorylation. FIG. 4C shows that the CRISPR-generated knockout cells for KCTD5 show increased staining for phospho-AKT when examined by flow-cytometry. FIG. 4D shows that restoration of KCTD5 expression in the CRISPR-generated knockout cells normalized AKT phosphorylation. These experiments demonstrate that new regulators of AKT phosphorylation can be identified and verified using CRISPR-generated gene inactivation and Western-Blot analysis. This demonstrates that the WD40-repeat E3-ligase KCTD5 is a new regulator of AKT phosphorylation.

Figure 5:
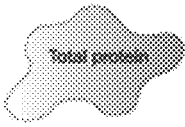
FIG. 5. Screening method is suitable for any intracellular phenotype that can be visualized and used to separate cell populations based on signal intensity.

FIG. 5 shows that the screening method according to the invention is suitable for any intracellular phenotype that can be visualized and used to separate cell populations based on signal intensity. This screening method, for example, using haploid mutagenized cells can in principle be used for any intracellular trait that can be quantified by separation methods like FACS (e.g. using total protein antibodies, post translational antibodies or labeled probes to quantify the expression or abundance of endogenous RNA molecules). The figure lists different readouts for intracellular phenotypes that could be applied to the screening approach.

Figure 6:
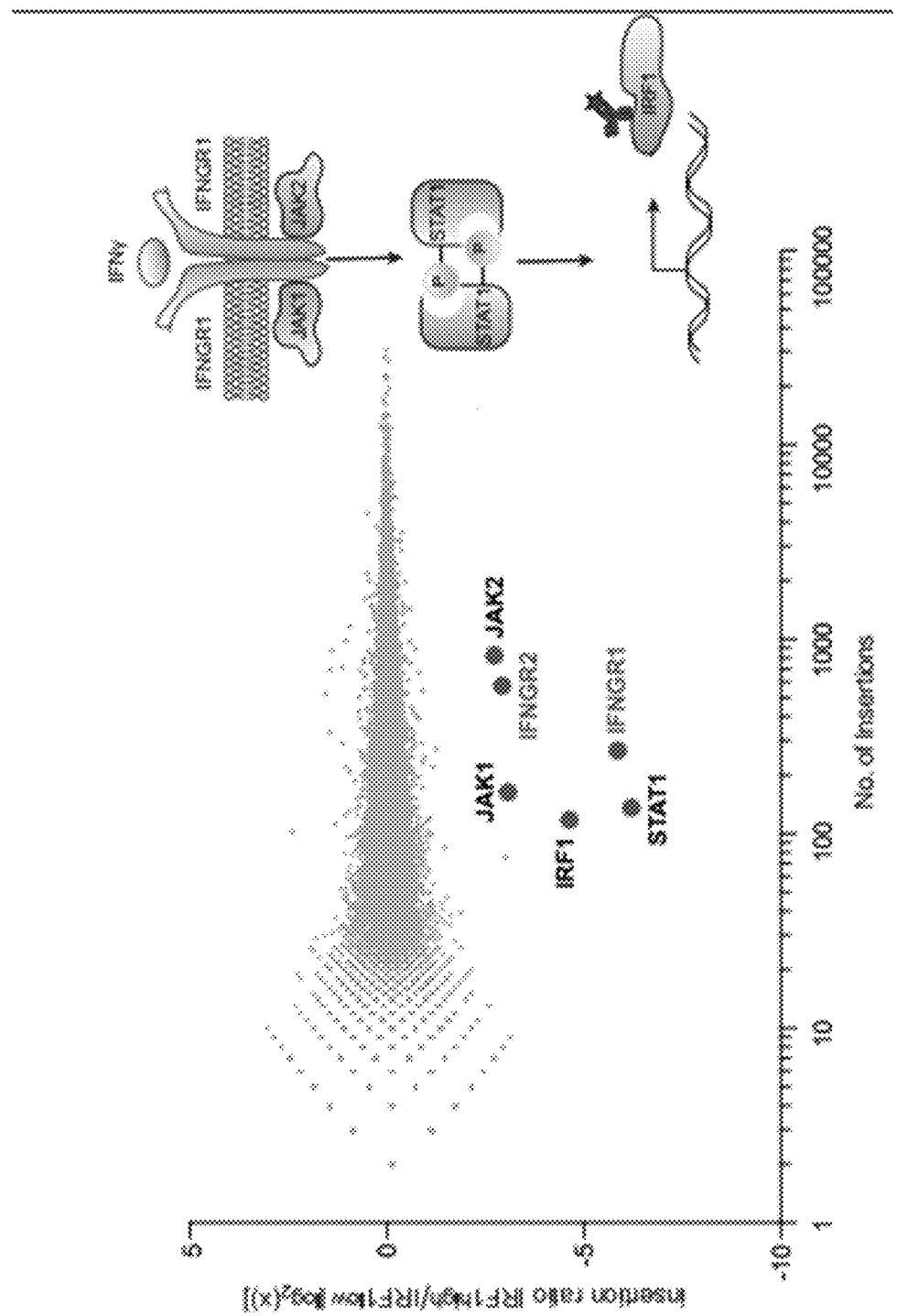
FIG. 6. A screen for IRF1 protein levels in cells stimulated with gamma interferon (protein expression).

FIG. 6 shows the results of a screen for IRF1 protein levels (protein expression). Haploid mutagenized cells were treated with Interferon gamma (IFN-γ) to induce IRF-1 expression. After 24 hours, cells were fixed, permeabilized and stained for IRF-1. Cells were sorted to enrich for populations showing 'high' or 'low' levels of IRF1 and subjected to deep sequencing of gene-trap insertion sites to identify mutants enriched in either cell population. Also shown is a scheme showing IFN-γ signaling pathway leading to IRF-1 transcription. Various genes labeled indicated (JAK1, JAK2, IRF1 and STAT1) were identified in the screen, employing the method according to the invention. Using this method allows to identify components of the IFN-γ signaling pathway.

Figure 7:
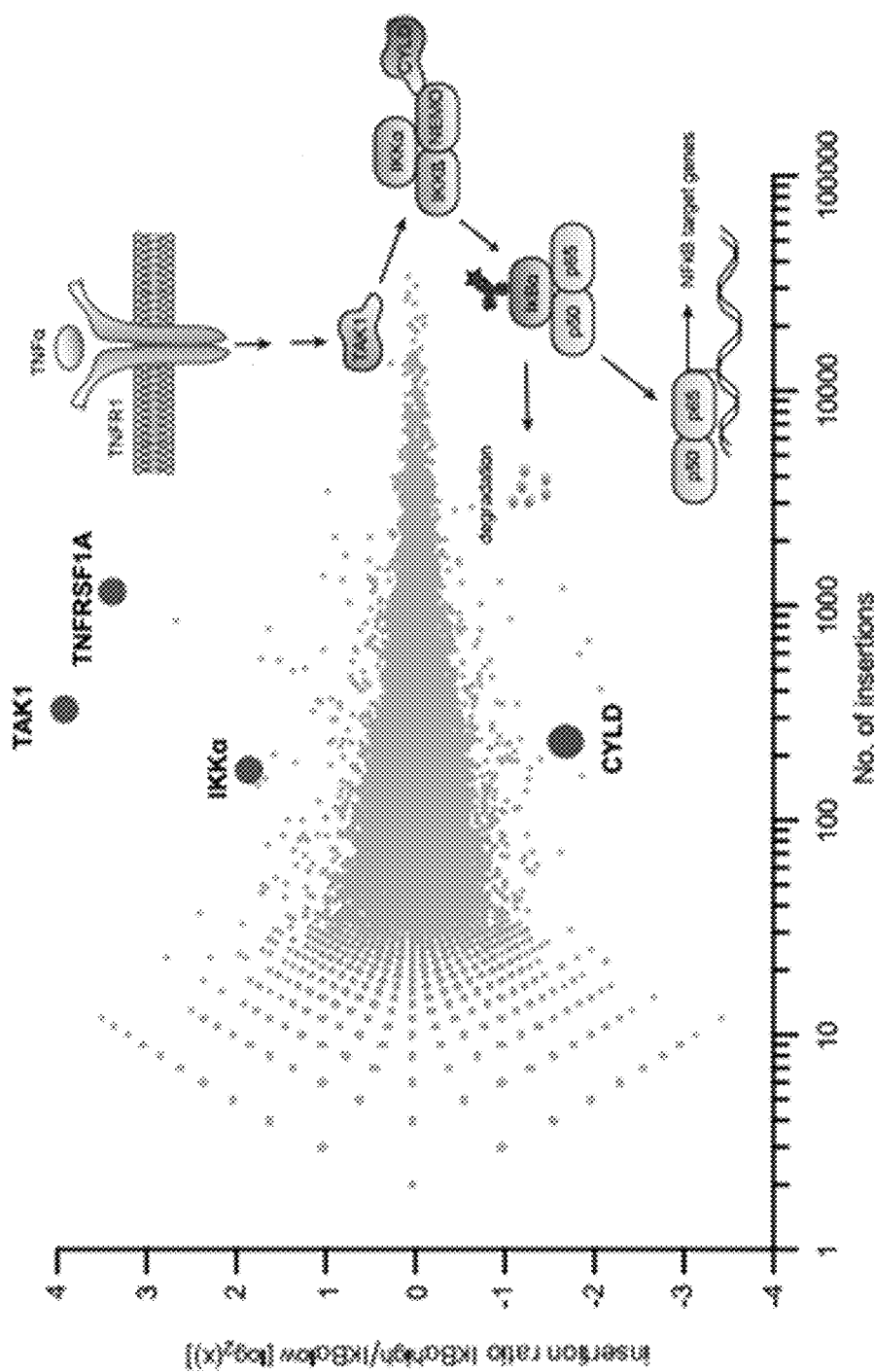
FIG. 7. A screen for IKBα expression (protein degradation).

FIG. 7 shows a screen for IkappaBalpha expression (protein degradation). Haploid HAP1 cells were mutagenized and treated with TNF-α for 30 min. After staining with specific IkappaBalpha antibodies, cells were sorted to enrich for populations with high and low IkappaBalpha intensity. To identify mutants that were enriched in either cell population gene-trap insertion sites were sequenced. Also shown is a scheme showing NFKB signaling components that were identified in the screen. This experiment demonstrates the application of a fixed-cell phenotypic screen on the NFKB signaling pathway. Known and unknown modifiers of the NFKB signaling could be identified.

Figure 8:
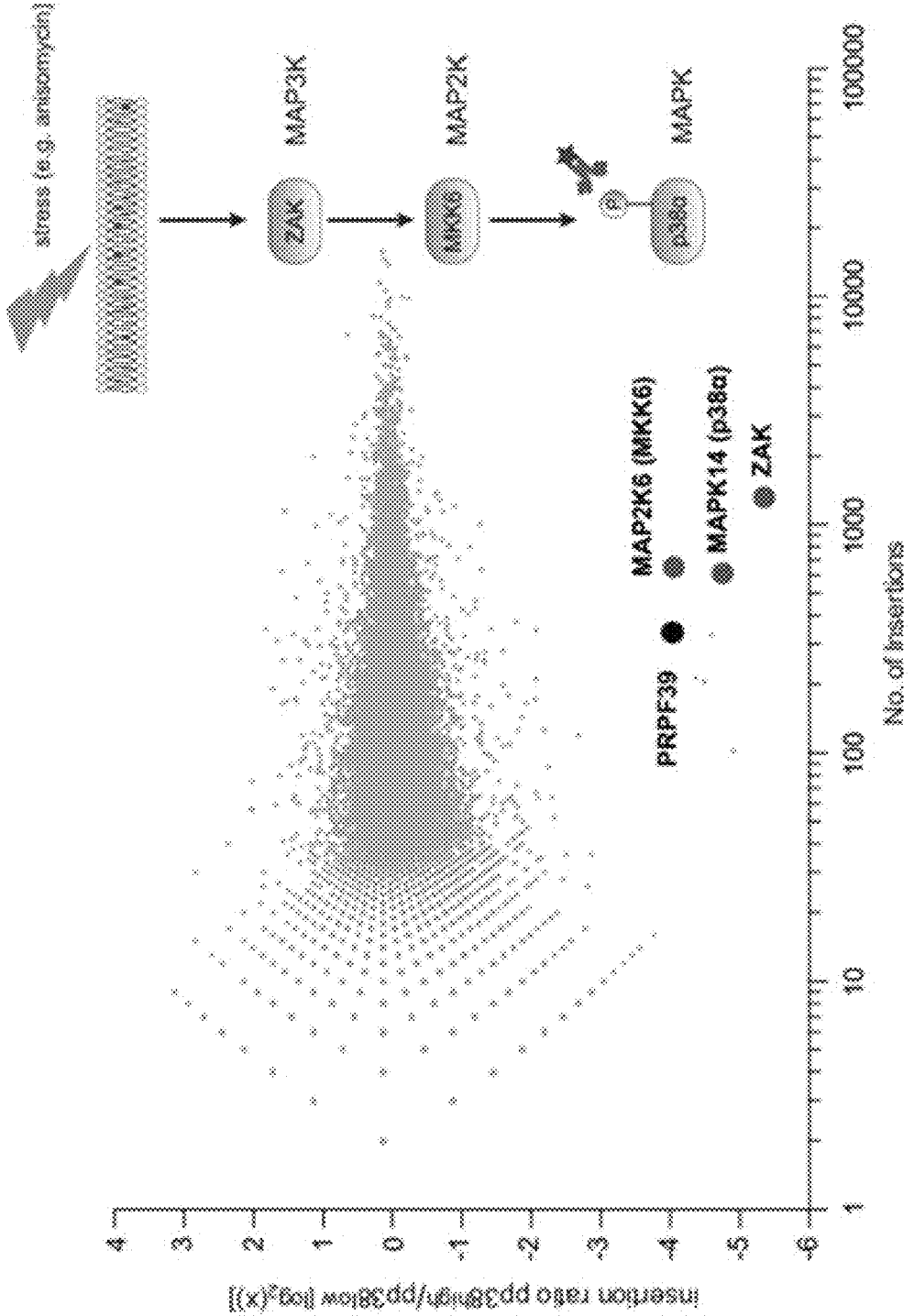
FIG. 8. A screen for p38 phosphorylation.

FIG. 8 shows a screen for p38 phosphorylation. Haploid mutagenized cells were treated with anisomycin to induce phosphorylation of p38a. After 4 hours, cells were fixed, permeabilized and stained with specific phosho-p38a antibodies. Cells were sorted to enrich for populations showing 'high' or 'low' levels of phospho-p38. Genomic DNA was isolated from both cell populations and used to map gene-trap insertion sites. Also shown is a scheme showing MAPK signaling pathway with genes that were identified in the screen. This experiment demonstrates the application of a fixed-cell phenotypic screen according to the invention on the MAPK signaling pathway. Known components are identified but also genes involved in RNA metabolism/splicing such as PRPF39.

Figure 9:
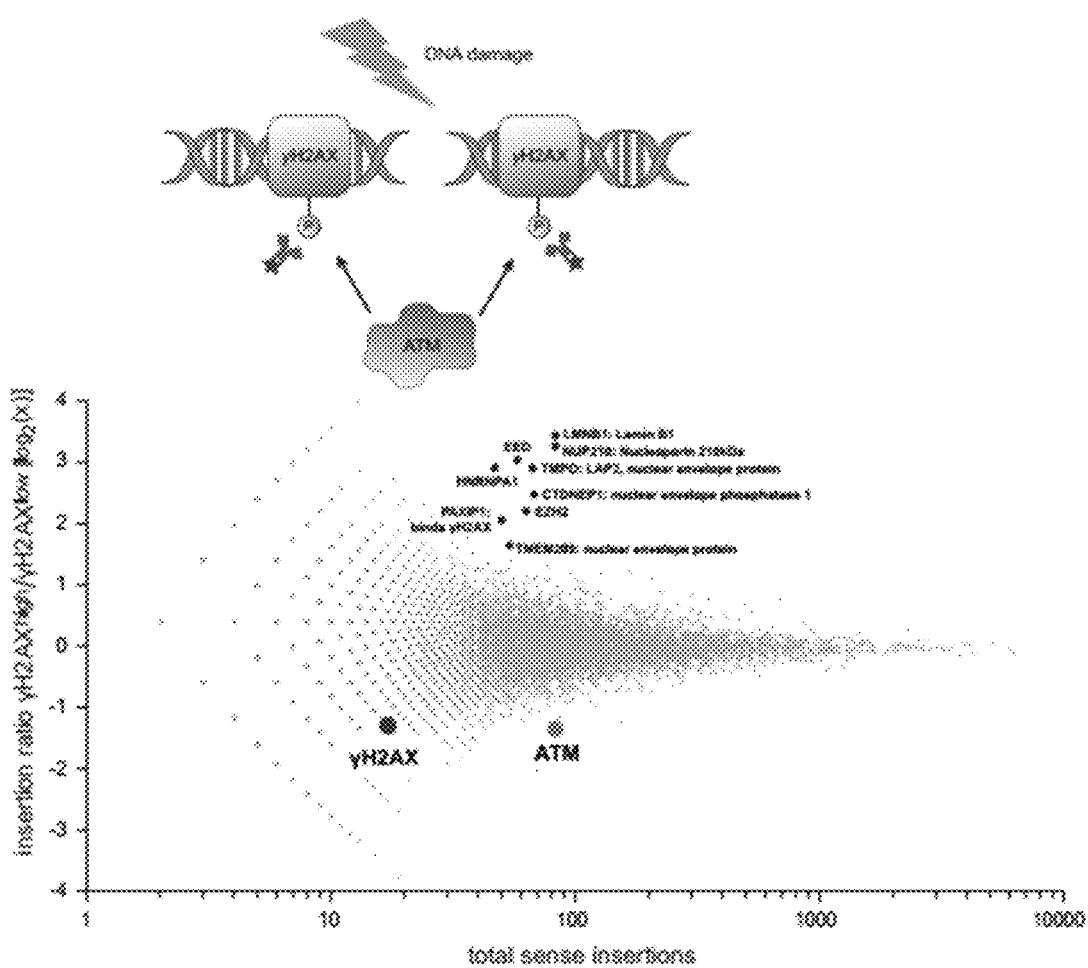
FIG. 9. A screen for DNA damage in irradiated cells.

FIG. 9 shows a screen for DNA damage in irradiated cells. Haploid mutagenized cells were exposed to ionizing radiation, fixed, permeabilized and stained for H2AX phosphorylation. As illustrated in the scheme, the histone protein H2AX is phosphorylated upon DNA damage. Cells were sorted to enrich for populations showing 'high' or 'low' levels of H2AX phosphorylation and subjected to deep sequencing of gene-trap insertion sites to identify mutants enriched in either cell population. This experiment demonstrates the application of a mutagenesis screen on non-viable permeabilized cells to study DNA damage signaling. Mutants with more H2AX phosphorylation (indicative of DNA damage) affect the nuclear matrix, nuclear pore and polycomb pathway suggesting a key role for nuclear organization in DNA damage.

Figure 10:
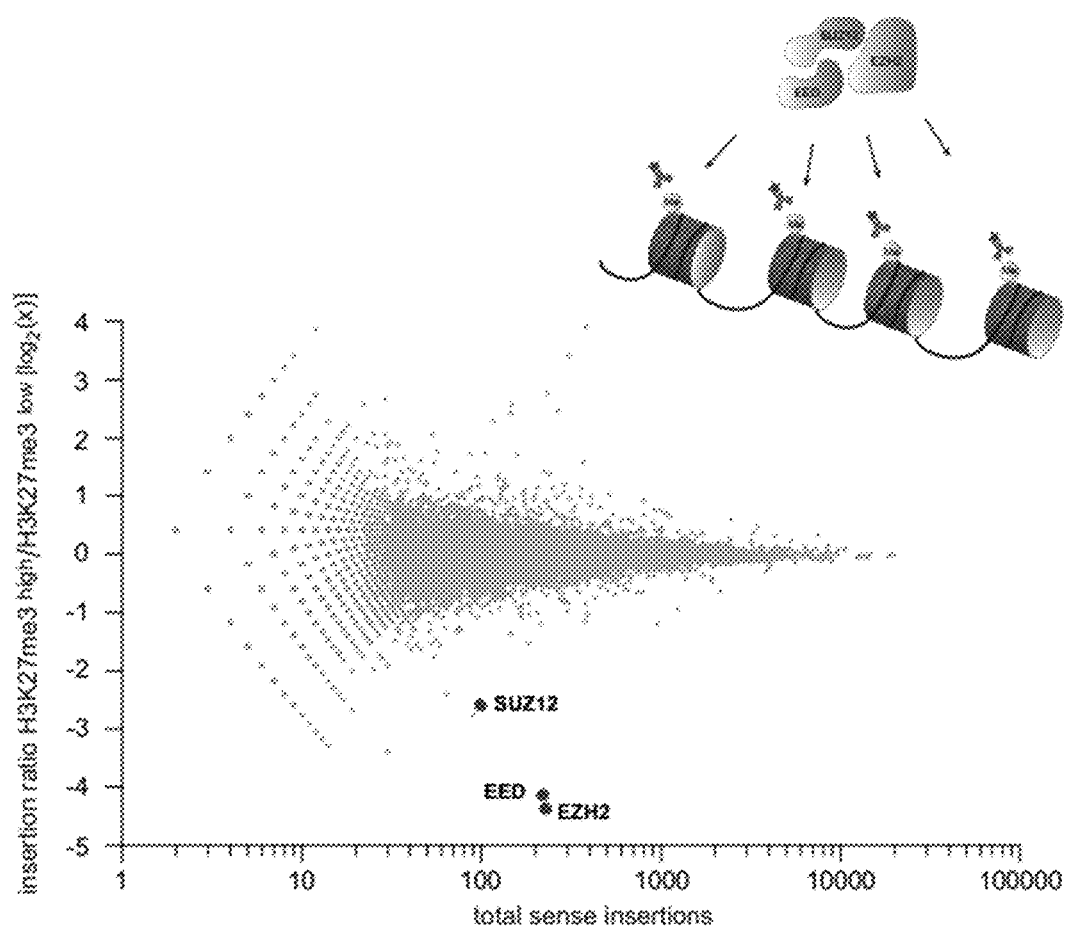
FIG. 10. A screen for a histone tail modification.
Figure 11A:
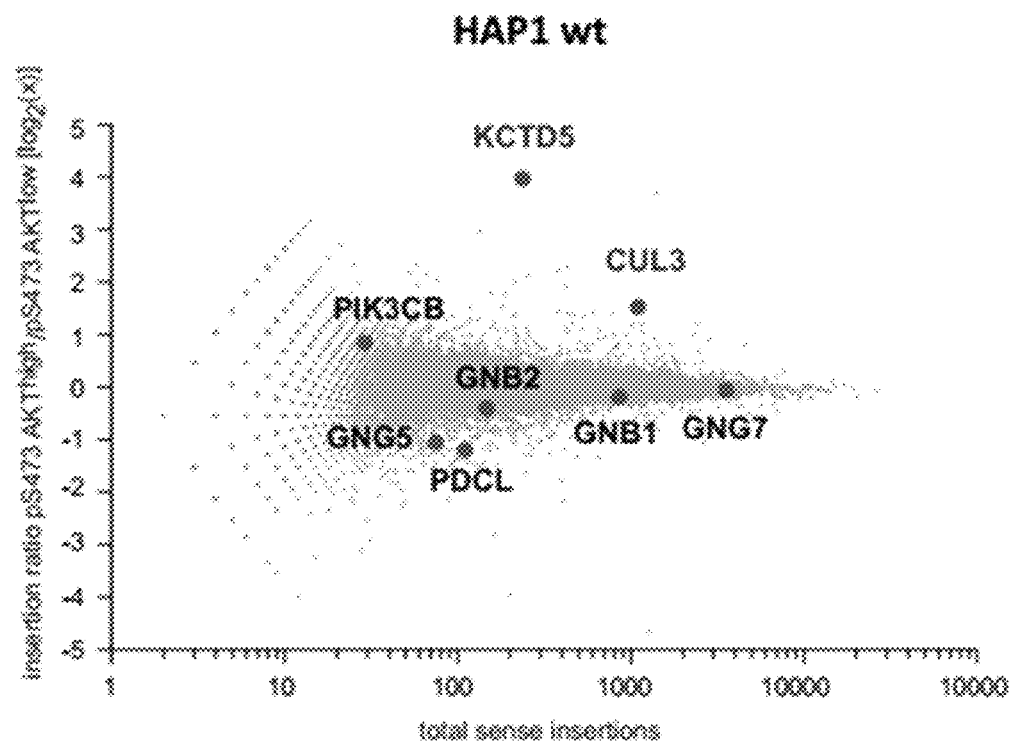
FIG. 11A. Identified genetic regulators that differentially affect AKT signaling in the presence or absence of KCTD5 labeled in the screen for AKT regulators in HAP1 wild type cells.
Figure 11B:
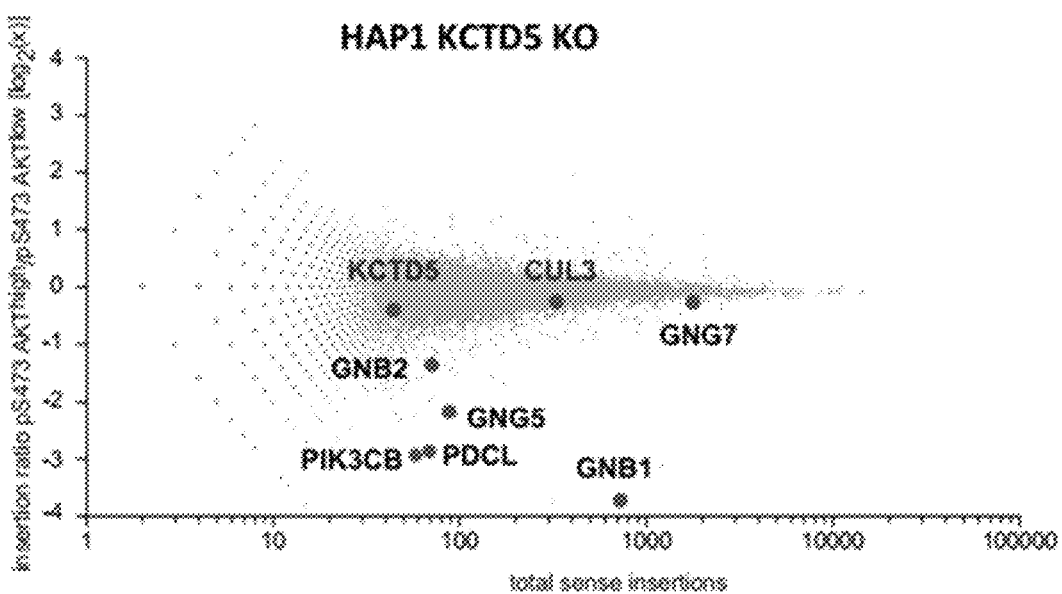
FIG. 11B. Identified genetic regulators that differentially affect AKT signaling in the presence or absence of KCTD5 labeled in the screen for AKT regulators in HAP1 KCTD5 KO cells.
Figure 11C:
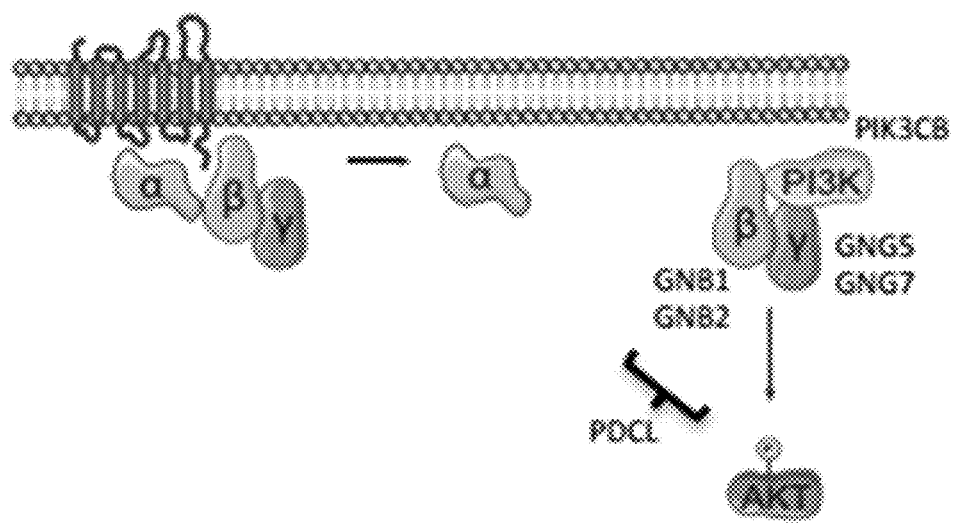
FIG. 11C. A scheme depicting the GPCR signaling components GNB1, GNB2, GNG5, GNG7, and PDCL.
Figure 11D:
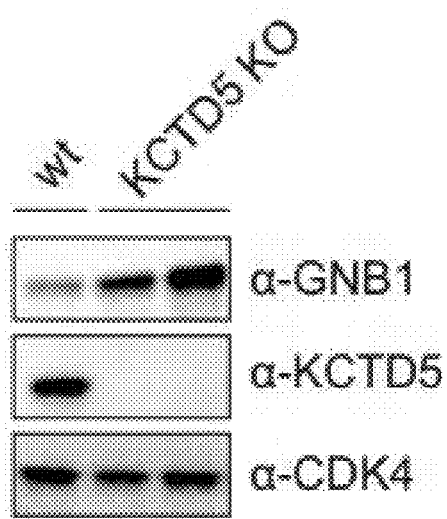
FIG. 11D. KCTD5 KO cells show an increased GNB1 protein expression compared to 293 wild-type cells as assessed by immunoblotting.

FIG. 10 shows a screen for a histone tail modification. Haploid mutagenized cells were fixed, permeabilized and stained for H3K27 trimethylation that is associated with transcriptional repression. Cells were sorted to enrich for populations showing 'high' or 'low' levels of H3K27 trimethylation, genomic DNA was isolated from both cell populations and used to map gene-trap insertion. This experiments shows that the method according to the invention gives insights into complexes regulating H3K27 trimethylation. The polycomb repressive complex 2 is known to be required for the generation of this modification and is composed of EZH2, SUZ12 and EED. All these components were identified in the screen.

FIG. 11 shows how KCTD5 modulates GPCR signaling. Figure A and B show a comparison of two genome-wide screens for AKT regulators (screen in HAP1 wt cells and KCTD5 KO cells) and reveal the pathway that activates AKT phosphorylation in the KCTD5 deficient cells. FIG. 11C shows a scheme for GPCR signaling. Identified components are highlighted (GNB1, GNB2, GNG5, GNG7, PDLC). FIG. 11D shows the E3-ligase KCTD5 leads to decreased protein levels of GNB1 (Guanine nucleotide-binding protein beta-1), a subunit of heterotrimeric G-proteins that are involved in GPCR signaling. KCTD5 KO cells show an increased GNB1 protein expression compared to 293 wild-type cells. The method according to the invention can identify genotype-specific modifiers of intracellular traits and can elucidate mechanisms responsible for mutant-associated phenotypes as well as enhancers or repressors of such phenotypes.

Figure 12:
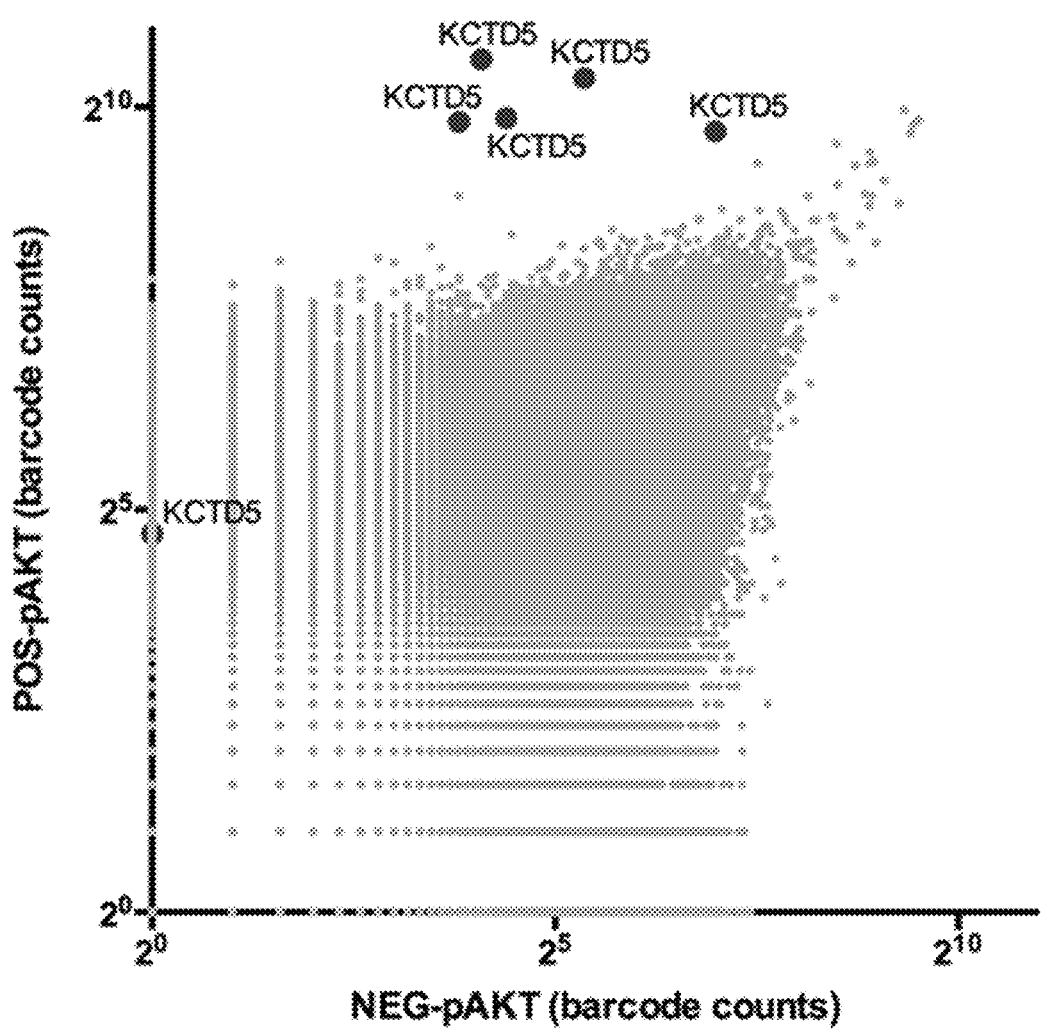
FIG. 12. A CRISPR/Cas9-based screen identifies KCTD5 as a negative regulator for phospho-AKT (pAKT).

FIG. 12 shows a CRISPR/Cas9-based screen identifies KCTD5 as a negative regulator for phospho AKT (pAKT). The lentiviral GeCKOv2 library (Sanjana et al. Nat. Methods 2014; containing ±123.000 guide RNA sequences) was introduced into HAP1 cells and populations with high and low pAKT levels were isolated. The abundance of each guide RNA (targeting its respective gene) in both cell populations were identified through PCR amplification and deep sequencing. For KCTD5, 5/6 gRNA sequences (indicated with KCTD5) were clearly enriched in the cell population with high pAKT levels. This shows that also mutagenesis using CRISPR/Cas9-based libraries can be used to study intracellular phenotypes in addition to gene-trap mutagenesis or other types of mutagenesis, for example in the HAP1 cells.

Figure 13:
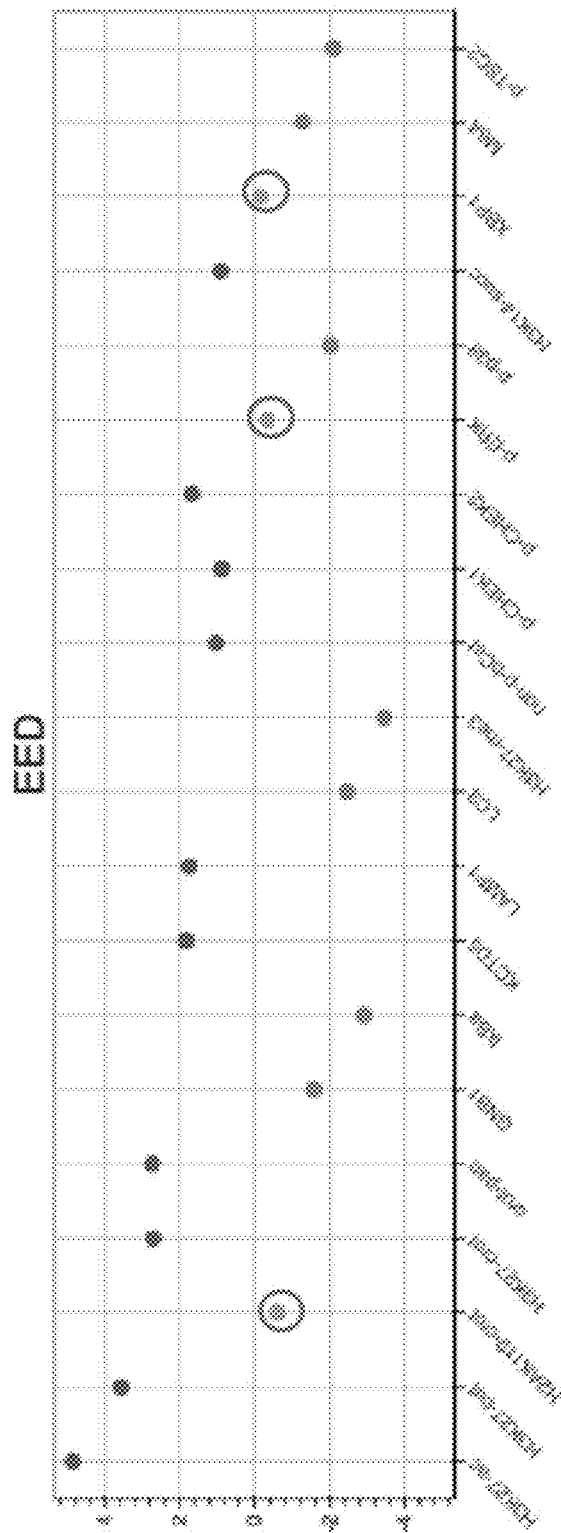
FIG. 13. Comparison of gene-associated phenotypes across a panel of phenotypes.

FIG. 13 shows a comparison of gene-associated phenotypes across a panel of phenotypes. Phenotypic readouts are listed on the x-axis. Mutation index is indicated on the Y-axis. Significant positive regulators have a negative value, and negative regulators have a positive value. In screens in which PRC2 (Polycomb Repressive Complex 2) subunits are not identified as significant regulators the data points are labeled with a circle. The complex has histone methyltransferase activity and primarily trimethylates histone H3 on lysine 27 (i.e. H3K27me3). By depositing the H3K27Me3 mark, the PRC2 complex are master regulators of gene expression and therefore are expected to affect many phenotypes across a wide variety of screens. This overview demonstrates that the three components of the PRC2 complex (EZH2, EED and SUZ12) show a near-identical phenotypic consequences across different screens. This comparative approach can be used to assign functions to genes.

Screens: H3K27-ac Histone 3 Lysine 27 acetyl; H3K27-but Histone 3 Lysine 27 butyryl; H2AK119-crot Histone 2A Lysine 119 crotonyl; H3K27-crot Histone 3 Lysine 27 crotonyl; crot-pan PAN Crotonyllysine; GNB1 abundance of Guanine Nucleotide Binding Protein, Beta polypeptide 1; IkKa abundance of Conserved Helix-Loop-Helix Ubiquitous Kinase; KCTD5 abundance of Potassium Channel Tetramerization Domain Containing 5; LAMP1 abundance of Lysosomal-Associated Membrane Protein 1; LC3 abundance of Microtubule-Associated Protein 1 Light Chain 3 Alpha, during starvation and chloroquine treatment; H3K27-me3 Histone 3 Lysine 27 trimethyl; non-p-bCat beta-Catenin unphosphorylated; p-CHEK1 phosphorylated Checkpoint Kinase 1; p-CHEK2 phosphorylated Checkpoint Kinase 2; p-ERK phosphorylated Mitogen-Activated Protein Kinase 1; p-p38 phosphorylated Mitogen-Activted Protein Kinase 14; H3K14-succ Histone 3 Lysine 14 succinyl; XBP1 X-Box Binding Protein abundance, induced with Thapsigargin; M6A N6-methyladenosine; p-TSC2 phosphorylated Tuberous Sclerosis 2

Figure 14:
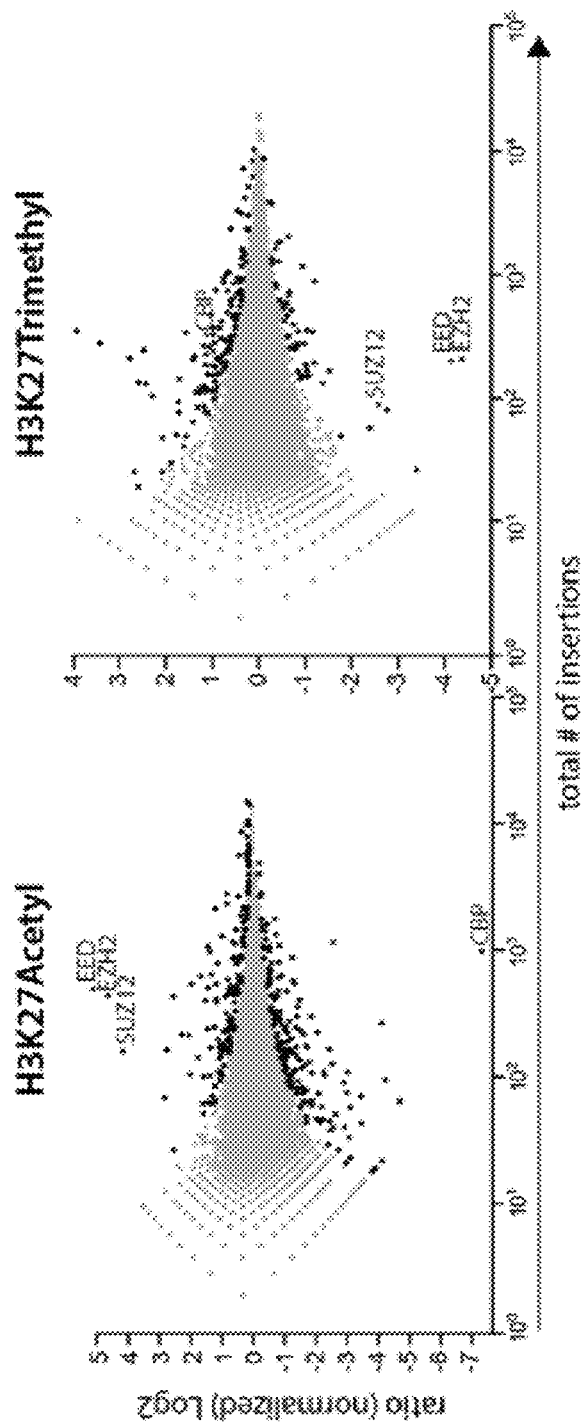
FIG. 14. Comparative analysis of genes required for two similar Post Translational Modifications (PTMs) at the same amino acid in a histone protein.

FIG. 14 shows a comparative analysis of genes required for two similar Post Translational Modifications (PTMs) at the same amino acid in a histone protein. Histone 3 Lysine 27 (H3K27) is known to be acetylated (by CREB Binding Protein, a mark associated with active chromatin), and tri-methylated (by the Polycomb Repressive Complex 2 (PRC2), associated with silenced chromatin). As these modifications affect the same residue, they are mutually exclusive and an increase in H3K27Ac leads to a decrease of the amount of H3K27Me3. This is also observed in the screens, where CBP is identified as a strong positive regulator of H3K27Ac and a negative regulator of H3K27Me3 and vice versa for the PRC2. Moreover, modification-specific genes can be identified.

Figure 15:
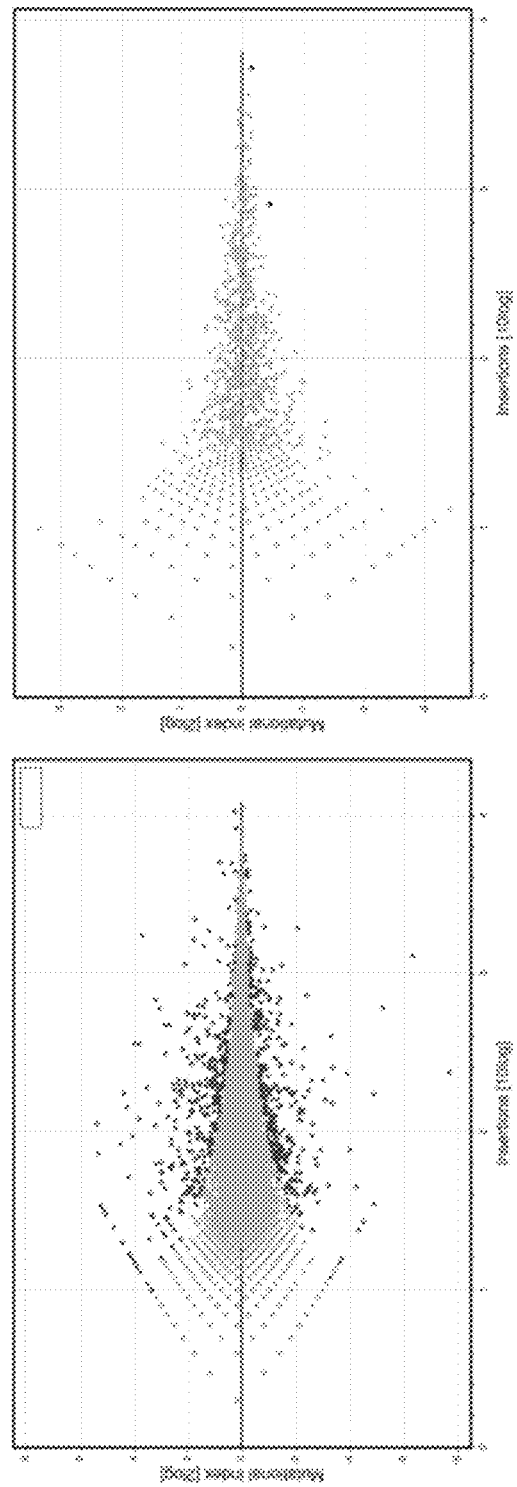
FIG. 15. Screen for lysosomal protein LAMP1 abundance. The same plot was redrawn only depicting the 3000 lowest expressed genes in HAP1 cells.

FIG. 15 shows a screen for lysosomal protein LAMP1 abundance. False-positive hits are very infrequent with the method of the invention. When considering RNA sequencing data of HAP1 cells and overlaying this on a screening dataset (left), the 3000 non- or lowest expressed genes (right) do not contribute to the query phenotype (right), as shown here for a screen for the abundance of lysosomal protein LAMP1 (left). This indicates the accuracy of the approach.

FIG. 16 shows that haploid genetic screens may identify genes that upon mutation alter the levels of a disease marker. The abundance of the 'disease marker' indicates aberrant cell physiology in the 'disease genotype'. (A) Mutagenized HAP1 cells were fixed, permeabilized and stained with an antibody that recognized the disease marker. Cells with low and high levels of the marker were sorted after which the mutation spectra in both populations were mapped as described. Mutation of several known disease-inducing genes results in elevated marker levels (unlabeled among top-outliers). (B) Mutagenized HAP1 cells deficient for a disease gene were stained and processed as described above. This 'suppressor' screen identifies the genes 1, 2 and 3 that upon inactivation lower the levels of the disease marker in context of disease gene deficiency, which mimics a heritable human syndrome.

The invention claimed is:

1. A method for identifying a genetic element that affects a phenotype of a cell, wherein said phenotype is manifested intracellularly, the method comprising the steps of:

(a) subjecting a pool of cells to mutagenesis treatment;

(b) fixating the pool of cells with a fixation reagent, and optionally with a cross-linking agent; and permeabilizing the pool of cells with a permeabilization reagent;

(c) treating the pool of cells with one or more detectable probe(s) selected from an antibody or a RNA probe to detect the affected phenotype;

(d) sorting the cells based on the detection of at least one of the one or more detectable probe(s) to obtain one or more population of cells;

(e) optionally, de-crosslinking the cells in each of the obtained populations of cells; and (f) sequencing the DNA and/or RNA of at least part of the obtained populations of cells to identify a genetic element that affects the phenotype of the cell.

2. The method of claim 1, wherein in step (d) at least two population of cells are obtained with the sorting of the cells based on the detection of at least one of the one or more detectable probes(s) and wherein in step (f) the DNA and/or RNA of at least two populations of cells are sequenced and compared to identify a genetic element that affects the phenotype of the cell.

3. The method of claim 1, wherein the genetic element is selected from the group consisting of a gene, an intron, an exon, a promoter and a noncoding RNA.

4. The method of claim 1, wherein the cell is selected from the group consisting of a eukaryotic cell, an animal cell, a plant cell, a yeast cell, a mammalian cell, a human cell, or a stem cell.

5. The method of claim 1, wherein the cell is a near-haploid cell or fully haploid cell.

6. The method of claim 1, wherein the mutagenesis is random mutagenesis.

7. The method of claim 1, wherein the mutagenesis comprises the use of radiation, mutagenic chemicals, insertion mutagenesis, or a CRISPR library of guide RNA sequences.

8. The method of claim 1, wherein the cells are exposed to a stress condition or growth condition and/or wherein the cells are treated with a compound before the cells are fixed and permeabilized in step (b).

9. The method of claim 1, wherein the fixation reagent to fix the cells is selected from the group consisting of cross-linking reagents and non-crosslinking reagents and wherein the permeabilization reagent is selected from the group consisting of solvents and detergents.

10. The method of claim 1, wherein the detectable probe binds to a protein, a post-translation modified protein, a lipid, DNA, RNA, or binds or detects a metabolite or cellular element.

11. The method of claim 1, wherein sorting comprises flow cytometry, FACS analysis, mass cytometry, or magnetic sorting.

12. The method of claim 1, wherein the probe comprises a detectable moiety selected from a fluorescent moiety, a radioactive moiety, magnetic moiety, and a label that can be measured using mass-spectrometry.

13. The method of claim 1, wherein the phenotype is manifested in the cytosol, inside an organelle, in the membrane of an organelle or in the cell membrane.

14. The method of claim 1, wherein the phenotype is increased protein abundance, decreased protein abundance, increased protein activity, decreased protein activity, increased post-translational modification of a protein, decreased post-translational expression of a protein, increased mRNA abundance or decreased mRNA abundance, wherein the increase or decrease is measured relative to the total population of the pool of cells subjected to mutagenesis treatment in step (a), and wherein an increase is defined as the highest 5% of the protein abundance, protein activity, post-translational modification of a protein, or mRNA abundance, and a decrease is defined as the lowest 5% of the protein abundance, protein activity, post-translational modification of a protein, or mRNA abundance.

15. The method of claim 1, wherein sequencing comprises high-throughput sequencing.

16. The method of claim 1, further comprising identifying a cellular element that is related to the genetic element identified.

17. A method for identifying a modulator of a gene product encoded by a candidate gene that affects a phenotype of a cell, wherein said phenotype is manifested intracellularly, the method comprising the steps of:
   (a) subjecting a pool of cells to mutagenesis treatment;
   (b) fixating of the pool of cells with a fixation reagent, and optionally with a cross-linking agent, and permeabilizing the pool of cells with a permeabilization reagent;
   (c) treating the pool of cells with one or more detectable probe(s) selected from an antibody or a RNA probe to detect the affected phenotype;
   (d) sorting the cells based on the detection of at least one of the one or more detectable probe(s) to obtain one or more population of cells,
   (e) optionally, de-crosslinking the cells in each of the obtained populations of cells;
   (f) sequencing the DNA and/or RNA of at least part of the obtained populations of cells to identify a genetic element that affects the phenotype of the cell, wherein the genetic element is a candidate gene;
   (g) identifying a modulator that affects expression or activity of an expression product of said identified candidate gene that affects the phenotype of the cell.

18. The method of claim 17, wherein in step (d) at least two population of cells are obtained with the sorting of the cells based on the detection of at least one of the one or more detectable probes(s) and wherein in step (f) the DNA and/or RNA of at least two populations of cells are sequenced and compared to identify a genetic elements that affects the phenotype of the cell.

19. The method of claim 17, wherein the method is used for establishing or analyzing biological pathways, for identifying genes involved in disease, for studying drug-target interaction, for studying drug-drug interaction, or to analyze suppression or modulation of a phenotype.

20. The method of claim 17, further comprising identifying a cellular element that is related to the genetic element identified.

* * * * *